US008865415B2

(12) United States Patent
Montgomery

(10) Patent No.: US 8,865,415 B2
(45) Date of Patent: *Oct. 21, 2014

(54) METHODS AND KITS FOR MEASURING VON WILLEBRAND FACTOR

(71) Applicants: Blood Center Research Foundation, Milwaukee, WI (US); The Medical College of Wisconsin, Inc., Milwaukee, WI (US)

(72) Inventor: Robert Montgomery, Cedarburg, WI (US)

(73) Assignees: Blood Center Research Foundation, Milwaukee, WI (US); The Medical College of Wisconsin, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/669,866

(22) Filed: Nov. 6, 2012

(65) Prior Publication Data

US 2013/0149716 A1 Jun. 13, 2013

Related U.S. Application Data

(63) Continuation of application No. 13/153,105, filed on Jun. 3, 2011, now Pat. No. 8,318,444, which is a continuation of application No. 12/197,057, filed on Aug. 22, 2008, now Pat. No. 8,163,496.

(60) Provisional application No. 60/957,604, filed on Aug. 23, 2007.

(51) Int. Cl.
*G01N 33/53* (2006.01)
*G01N 33/50* (2006.01)
*G01N 33/86* (2006.01)

(52) U.S. Cl.
CPC .......... *G01N 33/86* (2013.01); *G01N 2333/755* (2013.01); *G01N 33/5008* (2013.01); *G01N 2333/705* (2013.01)
USPC ............. 435/7.1; 435/7.21; 435/7.8; 530/350

(58) Field of Classification Search
None
See application file for complete search history.

(56) References Cited

U.S. PATENT DOCUMENTS 8,163,496 B2 * 4/2012 Montgomery ................. 435/7.1
8,318,444 B2 * 11/2012 Montgomery ................. 435/7.1

FOREIGN PATENT DOCUMENTS

WO WO 0102853 A2 * 1/2001

OTHER PUBLICATIONS

Tait et al., Blood. Sep. 15, 2001;98(6):1812-8.*
Federici et al., Hematologica, 2004, 89:77-85.*
Enayat et al., Thromb Haemost. Nov. 2012;108(5):946-54. doi: 10.1160/TH12-04-0189. Epub Sep. 26, 2012.*

* cited by examiner

*Primary Examiner* — Michael Szperka
(74) *Attorney, Agent, or Firm* — Quarles & Brady, LLP

(57) ABSTRACT

Methods and kits for measuring levels of von Willebrand factor function in a sample without using a platelet aggregation agonist, such as ristocetin, comprising recombinant glycoprotein Ibα having at least two of a G233V, D235Y and M239V mutations and an agent to detect a complex between the recombinant glycoprotein Ibα and von Willebrand factor.

11 Claims, 8 Drawing Sheets

```
                        SEQUENCE LISTING

<160> NUMBER OF SEQ ID NOS: 9

<210> SEQ ID NO 1
<211> LENGTH: 2463
<212> TYPE: DNA
<213> ORGANISM: Homo sapiens
<220> FEATURE:
<221> NAME/KEY: CDS
<222> LOCATION: (76)..(1992)
<220> FEATURE:
<221> NAME/KEY: sig_peptide
<222> LOCATION: (76)..(123)
<220> FEATURE:
<221> NAME/KEY: mat_peptide
<222> LOCATION: (124)..(1992)

<400> SEQUENCE: 1
gagagaagga cggagtcgag tggcaccta gaagacgctc tgtgccttcg gaggtctttc         60
tgcctgcctg tcctc atg cct ctc ctc ctc ttg ctg ctc ctg ctg cca agc       111
                Met Pro Leu Leu Leu Leu Leu Leu Leu Leu Pro Ser
                -15                 -10                  -5 ccc tta cac ccc cac ccc atc tgt gag gtc tcc aaa gtg gcc agc cac        159
Pro Leu His Pro His Pro Ile Cys Glu Val Ser Lys Val Ala Ser His
         -1  1                   5                      10 cta gaa gtg aac tgt gac aag agg aat ctg aca gcg ctg cct cca gac        207
Leu Glu Val Asn Cys Asp Lys Arg Asn Leu Thr Ala Leu Pro Pro Asp
             15                  20                  25 ctg ccg aaa gac aca acc atc ctc cac ctg agt gag aac ctc ctg tac        255
Leu Pro Lys Asp Thr Thr Ile Leu His Leu Ser Glu Asn Leu Leu Tyr
         30                  35                  40 acc ttc tcc ctg gca acc ctg atg cct tac act cgc ctc act cag ctg        303
Thr Phe Ser Leu Ala Thr Leu Met Pro Tyr Thr Arg Leu Thr Gln Leu
45                  50                  55                  60 aac cta gat agg tgc gag ctc acc aag ctc cag gtc gat ggg acg ctg        351
Asn Leu Asp Arg Cys Glu Leu Thr Lys Leu Gln Val Asp Gly Thr Leu
                 65                  70                  75 cca gtg ctg ggg acc ctg gat cta tcc cac aat cag ctg caa agc ctg        399
Pro Val Leu Gly Thr Leu Asp Leu Ser His Asn Gln Leu Gln Ser Leu
             80                  85                  90
```

-continued

| | | |
|---|---|---|
| ccc ttg cta ggg cag aca ctg cct gct ctc acc gtc ctg gac gtc tcc<br>Pro Leu Leu Gly Gln Thr Leu Pro Ala Leu Thr Val Leu Asp Val Ser<br>95                               100                          105 | 447 | |
| ttc aac cgg ctg acc tcg ctg cct ctt ggt gcc ctg cgt ggt ctt ggc<br>Phe Asn Arg Leu Thr Ser Leu Pro Leu Gly Ala Leu Arg Gly Leu Gly<br>110                              115                          120 | 495 | |
| gaa ctc caa gag ctc tac ctg aaa ggc aat gag ctg aag acc ctg ccc<br>Glu Leu Gln Glu Leu Tyr Leu Lys Gly Asn Glu Leu Lys Thr Leu Pro<br>125                               130                          135                          140 | 543 | |
| cca ggg ctc ctg acg ccc aca ccc aag ctg gag aag ctc agt ctg gct<br>Pro Gly Leu Leu Thr Pro Thr Pro Lys Leu Glu Lys Leu Ser Leu Ala<br>                         145                          150                          155 | 591 | |
| aac aac aac ttg act gag ctc ccc gct ggg ctc ctg aat ggg ctg gag<br>Asn Asn Asn Leu Thr Glu Leu Pro Ala Gly Leu Leu Asn Gly Leu Glu<br>                             160                          165                          170 | 639 | |
| aat ctc gac acc ctt ctc ctc caa gag aac tcg ctg tat aca ata cca<br>Asn Leu Asp Thr Leu Leu Leu Gln Glu Asn Ser Leu Tyr Thr Ile Pro<br>                     175                             180                          185 | 687 | |
| aag ggc ttt ttt ggg tcc cac ctc ctg cct ttt gct ttt ctc cac ggg<br>Lys Gly Phe Phe Gly Ser His Leu Leu Pro Phe Ala Phe Leu His Gly<br>190                               195                          200 | 735 | |
| aac ccc tgg tta tgc aac tgt gag atc ctc tat ttt cgt cgc tgg ctg<br>Asn Pro Trp Leu Cys Asn Cys Glu Ile Leu Tyr Phe Arg Arg Trp Leu<br>205                               210                          215                          220 | 783 | |
| cag gac aat gct gaa aat gtc tac gta tgg aag caa ggt gtg gac gtc<br>Gln Asp Asn Ala Glu Asn Val Tyr Val Trp Lys Gln Gly Val Asp Val<br>                         225                          230                          235 | 831 | |
| aag gcc atg acc tct aat gtg gcc agt gtg cag tgt gac aat tca gac<br>Lys Ala Met Thr Ser Asn Val Ala Ser Val Gln Cys Asp Asn Ser Asp<br>240                               245                          250 | 879 | |
| aag ttt ccc gtc tac aaa tac cca gga aag ggg tgc ccc acc ctt ggt<br>Lys Phe Pro Val Tyr Lys Tyr Pro Gly Lys Gly Cys Pro Thr Leu Gly<br>                       255                          260                          265 | 927 | |
| gat gaa ggt gac aca gac cta tat gat tac tac cca gaa gag gac act<br>Asp Glu Gly Asp Thr Asp Leu Tyr Asp Tyr Tyr Pro Glu Glu Asp Thr<br>270                               275                          280 | 975 | |
| gag ggc gat aag gtg cgt gcc aca agg act gtg gtc aag ttc ccc acc<br>Glu Gly Asp Lys Val Arg Ala Thr Arg Thr Val Val Lys Phe Pro Thr<br>285                               290                          295                          300 | 1023 | |
| aaa gcc cat aca acc ccc tgg ggt cta ttc tac tca tgg tcc act gct<br>Lys Ala His Thr Thr Pro Trp Gly Leu Phe Tyr Ser Trp Ser Thr Ala<br>                       305                          310                          315 | 1071 | |
| tct cta gac agc caa atg ccc tcc tcc ttg cat cca aca caa gaa tcc<br>Ser Leu Asp Ser Gln Met Pro Ser Ser Leu His Pro Thr Gln Glu Ser<br>                       320                          325                          330 | 1119 | |
| act aag gag cag acc aca ttc cca cct aga tgg acc cca aat ttc aca<br>Thr Lys Glu Gln Thr Thr Phe Pro Pro Arg Trp Thr Pro Asn Phe Thr<br>                       335                          340                          345 | 1167 | |
| ctt cac atg gaa tcc atc aca ttc tcc aaa act cca aaa tcc act act<br>Leu His Met Glu Ser Ile Thr Phe Ser Lys Thr Pro Lys Ser Thr Thr<br>350                               355                          360 | 1215 | |
| gaa cca acc cca agc ccg acc acc tca gag ccc gtc ccg gag ccc gcc<br>Glu Pro Thr Pro Ser Pro Thr Thr Ser Glu Pro Val Pro Glu Pro Ala<br>365                               370                          375                          380 | 1263 | |
| cca aac atg acc acc ctg gag ccc act cca agc ccg acc acc cca gag<br>Pro Asn Met Thr Thr Leu Glu Pro Thr Pro Ser Pro Thr Thr Pro Glu<br>                       385                          390                          395 | 1311 | |
| ccc acc tca gag ccc gcc ccc agc ccg acc acc ccg gag ccc acc tca<br>Pro Thr Ser Glu Pro Ala Pro Ser Pro Thr Thr Pro Glu Pro Thr Ser<br>                       400                          405                          410 | 1359 | |

| | | | | | | | | | | | | | | | |
|---|---|---|---|---|---|---|---|---|---|---|---|---|---|---|---|
| gag | ccc | gcc | ccc | agc | ccg | acc | acc | ccg | gag | ccc | acc | cca | atc | ccg | acc | 1407 |
| Glu | Pro | Ala | Pro | Ser | Pro | Thr | Thr | Pro | Glu | Pro | Thr | Pro | Ile | Pro | Thr | |
| | | 415 | | | | 420 | | | | 425 | | | | | | |

| atc | gcc | aca | agc | ccg | acc | atc | ctg | gtg | tct | gcc | aca | agc | ctg | atc | act | 1455 |
| Ile | Ala | Thr | Ser | Pro | Thr | Ile | Leu | Val | Ser | Ala | Thr | Ser | Leu | Ile | Thr | |
| 430 | | | | | 435 | | | | | 440 | | | | | | |

| cca | aaa | agc | aca | ttt | tta | act | acc | aca | aaa | ccc | gta | tca | ctc | tta | gaa | 1503 |
| Pro | Lys | Ser | Thr | Phe | Leu | Thr | Thr | Thr | Lys | Pro | Val | Ser | Leu | Leu | Glu | |
| 445 | | | | 450 | | | | | 455 | | | | | 460 | | |

| tcc | acc | aaa | aaa | acc | atc | cct | gaa | ctt | gat | cag | cca | cca | aag | ctc | cgt | 1551 |
| Ser | Thr | Lys | Lys | Thr | Ile | Pro | Glu | Leu | Asp | Gln | Pro | Pro | Lys | Leu | Arg | |
| | | | 465 | | | | | 470 | | | | | 475 | | | |

| ggg | gtg | ctc | caa | ggg | cat | ttg | gag | agc | tcc | aga | aat | gac | cct | ttt | ctc | 1599 |
| Gly | Val | Leu | Gln | Gly | His | Leu | Glu | Ser | Ser | Arg | Asn | Asp | Pro | Phe | Leu | |
| | | | 480 | | | | | 485 | | | | | 490 | | | |

| cac | ccc | gac | ttt | tgc | tgc | ctc | ctc | ccc | ctg | ggc | ttc | tat | gtc | ttg | ggt | 1647 |
| His | Pro | Asp | Phe | Cys | Cys | Leu | Leu | Pro | Leu | Gly | Phe | Tyr | Val | Leu | Gly | |
| | | 495 | | | | | 500 | | | | | 505 | | | | |

| ctc | ttc | tgg | ctg | ctc | ttt | gcc | tct | gtg | gtc | ctc | atc | ctg | ctg | ctg | agc | 1695 |
| Leu | Phe | Trp | Leu | Leu | Phe | Ala | Ser | Val | Val | Leu | Ile | Leu | Leu | Leu | Ser | |
| | 510 | | | | | 515 | | | | | 520 | | | | | |

| tgg | gtt | ggg | cat | gtg | aaa | cca | cag | gcc | ctg | gac | tct | ggc | caa | ggt | gct | 1743 |
| Trp | Val | Gly | His | Val | Lys | Pro | Gln | Ala | Leu | Asp | Ser | Gly | Gln | Gly | Ala | |
| 525 | | | | | 530 | | | | | 535 | | | | | 540 | |

| gct | ctg | acc | aca | gcc | aca | caa | acc | aca | cac | ctg | gag | ctg | cag | agg | gga | 1791 |
| Ala | Leu | Thr | Thr | Ala | Thr | Gln | Thr | Thr | His | Leu | Glu | Leu | Gln | Arg | Gly | |
| | | | | 545 | | | | | 550 | | | | | 555 | | |

| cgg | caa | gtg | aca | gtg | ccc | cgg | gcc | tgg | ctg | ctc | ttc | ctt | cga | ggt | tcg | 1839 |
| Arg | Gln | Val | Thr | Val | Pro | Arg | Ala | Trp | Leu | Leu | Phe | Leu | Arg | Gly | Ser | |
| | | | 560 | | | | | 565 | | | | | 570 | | | |

| ctt | ccc | act | ttc | cgc | tcc | agc | ctc | ttc | ctg | tgg | gta | cgg | cct | aat | ggc | 1887 |
| Leu | Pro | Thr | Phe | Arg | Ser | Ser | Leu | Phe | Leu | Trp | Val | Arg | Pro | Asn | Gly | |
| | | 575 | | | | | 580 | | | | | 585 | | | | |

| cgt | gtg | ggg | cct | cta | gtg | gca | gga | agg | agg | ccc | tca | gct | ctg | agt | cag | 1935 |
| Arg | Val | Gly | Pro | Leu | Val | Ala | Gly | Arg | Arg | Pro | Ser | Ala | Leu | Ser | Gln | |
| | 590 | | | | | 595 | | | | | 600 | | | | | |

| ggt | cgt | ggt | cag | gac | ctg | ctg | agc | aca | gtg | agc | att | agg | tac | tct | ggc | 1983 |
| Gly | Arg | Gly | Gln | Asp | Leu | Leu | Ser | Thr | Val | Ser | Ile | Arg | Tyr | Ser | Gly | |
| 605 | | | | 610 | | | | | 615 | | | | | 620 | | |

| cac | agc | ctc | tgagggtggg | aggtttgggg | accttgagag | aagagcctgt | | | | | | | | | | 2032 |
| His | Ser | Leu | | | | | | | | | | | | | | | gggctctcct attggaatct agttgggggt tggaggggta aggaacacag ggtgataggg  2092 gaggggtctt agttcctttt tctgtatcag aagccctgtc ttcacaacac aggcacacaa  2152 tttcagtccc agccaaagca gaaggggtaa tgacatggac ttggcggggg gacaagacaa  2212 agctcccgat gctgcatggg gcgctgccag atctcacggt gaaccatttt ggcagaatac  2272 agcatggttc ccacatgcat ctatgcacag aagaaaatct ggaaagtgat ttatcaggat  2332 gtgagcactc gttgtgtctg gatgttacaa atatgggtgg ttttatttc ttttccctg  2392 tttagcattt tctagttttc cactattatt gtatattatc tgtataataa aaaataattt  2452 tagggttggg a  2463

<210> SEQ ID NO 2
<211> LENGTH: 639
<212> TYPE: PRT
<213> ORGANISM: Homo sapiens

<400> SEQUENCE: 2

```
Met Pro Leu Leu Leu Leu Leu Leu Leu Pro Ser Pro Leu His Pro
-15                 -10                  -5                  -1

His Pro Ile Cys Glu Val Ser Lys Val Ala Ser His Leu Glu Val Asn
  1          5                  10                 15

Cys Asp Lys Arg Asn Leu Thr Ala Leu Pro Pro Asp Leu Pro Lys Asp
             20              25                  30

Thr Thr Ile Leu His Leu Ser Glu Asn Leu Leu Tyr Thr Phe Ser Leu
             35              40                  45

Ala Thr Leu Met Pro Tyr Thr Arg Leu Thr Gln Leu Asn Leu Asp Arg
     50              55              60

Cys Glu Leu Thr Lys Leu Gln Val Asp Gly Thr Leu Pro Val Leu Gly
 65              70              75                  80

Thr Leu Asp Leu Ser His Asn Gln Leu Gln Ser Leu Pro Leu Leu Gly
             85              90                  95

Gln Thr Leu Pro Ala Leu Thr Val Leu Asp Val Ser Phe Asn Arg Leu
             100             105                 110

Thr Ser Leu Pro Leu Gly Ala Leu Arg Gly Leu Gly Glu Leu Gln Glu
             115             120                 125

Leu Tyr Leu Lys Gly Asn Glu Leu Lys Thr Leu Pro Pro Gly Leu Leu
     130             135                 140

Thr Pro Thr Pro Lys Leu Glu Lys Leu Ser Leu Ala Asn Asn Asn Leu
145             150             155                 160

Thr Glu Leu Pro Ala Gly Leu Leu Asn Gly Leu Glu Asn Leu Asp Thr
             165             170                 175

Leu Leu Leu Gln Glu Asn Ser Leu Tyr Thr Ile Pro Lys Gly Phe Phe
             180             185                 190

Gly Ser His Leu Leu Pro Phe Ala Phe Leu His Gly Asn Pro Trp Leu
         195             200             205

Cys Asn Cys Glu Ile Leu Tyr Phe Arg Arg Trp Leu Gln Asp Asn Ala
210             215             220

Glu Asn Val Tyr Val Trp Lys Gln Gly Val Asp Val Lys Ala Met Thr
225             230             235                 240

Ser Asn Val Ala Ser Val Gln Cys Asp Asn Ser Asp Lys Phe Pro Val
             245             250                 255

Tyr Lys Tyr Pro Gly Lys Gly Cys Pro Thr Leu Gly Asp Glu Gly Asp
             260             265                 270

Thr Asp Leu Tyr Asp Tyr Tyr Pro Glu Glu Asp Thr Glu Gly Asp Lys
     275             280             285

Val Arg Ala Thr Arg Thr Val Val Lys Phe Pro Thr Lys Ala His Thr
     290             295             300

Thr Pro Trp Gly Leu Phe Tyr Ser Trp Ser Thr Ala Ser Leu Asp Ser
305             310             315                 320

Gln Met Pro Ser Ser Leu His Pro Thr Gln Glu Ser Thr Lys Glu Gln
             325             330                 335

Thr Thr Phe Pro Pro Arg Trp Thr Pro Asn Phe Thr Leu His Met Glu
             340             345                 350

Ser Ile Thr Phe Ser Lys Thr Pro Lys Ser Thr Glu Pro Thr Pro
             355             360                 365

Ser Pro Thr Thr Ser Glu Pro Val Pro Glu Pro Ala Pro Asn Met Thr
     370             375             380

Thr Leu Glu Pro Thr Pro Ser Pro Thr Thr Pro Glu Pro Thr Ser Glu
385             390             395                 400
```

```
Pro Ala Pro Ser Pro Thr Thr Pro Glu Pro Thr Ser Glu Pro Ala Pro
            405                 410                 415
Ser Pro Thr Thr Pro Glu Pro Thr Pro Ile Pro Thr Ile Ala Thr Ser
        420                 425                 430
Pro Thr Ile Leu Val Ser Ala Thr Ser Leu Ile Thr Pro Lys Ser Thr
            435                 440                 445
Phe Leu Thr Thr Thr Lys Pro Val Ser Leu Leu Glu Ser Thr Lys Lys
    450                 455                 460
Thr Ile Pro Glu Leu Asp Gln Pro Pro Lys Leu Arg Gly Val Leu Gln
465                 470                 475                 480
Gly His Leu Glu Ser Ser Arg Asn Asp Pro Phe Leu His Pro Asp Phe
                485                 490                 495
Cys Cys Leu Leu Pro Leu Gly Phe Tyr Val Leu Gly Leu Phe Trp Leu
            500                 505                 510
Leu Phe Ala Ser Val Val Leu Ile Leu Leu Ser Trp Val Gly His
        515                 520                 525
Val Lys Pro Gln Ala Leu Asp Ser Gly Gln Gly Ala Ala Leu Thr Thr
    530                 535                 540
Ala Thr Gln Thr Thr His Leu Glu Leu Gln Arg Gly Arg Gln Val Thr
545                 550                 555                 560
Val Pro Arg Ala Trp Leu Leu Phe Leu Arg Gly Ser Leu Pro Thr Phe
                565                 570                 575
Arg Ser Ser Leu Phe Leu Trp Val Arg Pro Asn Gly Arg Val Gly Pro
            580                 585                 590
Leu Val Ala Gly Arg Arg Pro Ser Ala Leu Ser Gln Gly Arg Gly Gln
        595                 600                 605
Asp Leu Leu Ser Thr Val Ser Ile Arg Tyr Ser Gly His Ser Leu
    610                 615                 620

<210> SEQ ID NO 3
<211> LENGTH: 958
<212> TYPE: DNA
<213> ORGANISM: Homo sapiens
<220> FEATURE:
<221> NAME/KEY: CDS
<222> LOCATION: (28)..(645)

<400> SEQUENCE: 3
agtaagccgg gctgccgtct tctcgcc atg ggc tcc ggg ccg cgc ggg gcg ctg     54
                               Met Gly Ser Gly Pro Arg Gly Ala Leu
                                 1               5 agc tta ctg ctc ctg ctg ctg gcc ccg ccg agc cgc ccg gcc gca ggt      102
Ser Leu Leu Leu Leu Leu Leu Ala Pro Pro Ser Arg Pro Ala Ala Gly
 10                  15                  20                  25 tgc ccg gcg ccc tgt agc tgc gcg ggg acg ctc gtg gac tgc ggg cgc      150
Cys Pro Ala Pro Cys Ser Cys Ala Gly Thr Leu Val Asp Cys Gly Arg
                 30                  35                  40 cgc ggg ctg act tgg gcc tcg ctg ccc acc gcc ttc cct gtc gac aca      198
Arg Gly Leu Thr Trp Ala Ser Leu Pro Thr Ala Phe Pro Val Asp Thr
             45                  50                  55 acc gag ctg gtg ctg acc ggc aac aac ctg acg gcg ctg ccg ccg ggg      246
Thr Glu Leu Val Leu Thr Gly Asn Asn Leu Thr Ala Leu Pro Pro Gly
         60                  65                  70 ctg ctg gac gcg ctg ccc gcg ctg cgc acc gca cac ctg ggc gcc aac      294
Leu Leu Asp Ala Leu Pro Ala Leu Arg Thr Ala His Leu Gly Ala Asn
     75                  80                  85 ccc tgg cgc tgc gac tgc cgc ctt gtg ccg ctg cgc gcc tgg ctg gcc      342
Pro Trp Arg Cys Asp Cys Arg Leu Val Pro Leu Arg Ala Trp Leu Ala
```

```
                 90                  95                 100                105
   ggc cgc ccc gag cgt gcg ccc tac cgc gac ctg cgt tgc gtg gcg ccc          390
   Gly Arg Pro Glu Arg Ala Pro Tyr Arg Asp Leu Arg Cys Val Ala Pro
                    110                 115                 120 cca gcg ctg cgc ggc cgc ctg ctg ccc tat ctg gcc gag gac gag ctg          438
   Pro Ala Leu Arg Gly Arg Leu Leu Pro Tyr Leu Ala Glu Asp Glu Leu
               125                 130                 135 cgc gcc gct tgc gct ccc ggc ccg ctc tgc tgg ggg gcg ctg gcg gcg          486
   Arg Ala Ala Cys Ala Pro Gly Pro Leu Cys Trp Gly Ala Leu Ala Ala
           140                 145                 150 cag ctt gcg ctg ctg ggc ctt ggg ctg ctg cac gcg ttg ctg ctg gtg          534
   Gln Leu Ala Leu Leu Gly Leu Gly Leu Leu His Ala Leu Leu Leu Val
       155                 160                 165 ctg ctg ctg tgc cgc ctg cgg agg ctg cgg gcc cgg gcc cgc gct cgc          582
   Leu Leu Leu Cys Arg Leu Arg Arg Leu Arg Ala Arg Ala Arg Ala Arg
   170                 175                 180                 185 gcc gca gcc cgg ctg tcg ctg acc gac ccg ctg gtg gcc gag cga gcc          630
   Ala Ala Ala Arg Leu Ser Leu Thr Asp Pro Leu Val Ala Glu Arg Ala
                       190                 195                 200 gga acc gac gag tcc tgaggagaga accggtgcgt cctgaggaga gaaccggcgc          685
   Gly Thr Asp Glu Ser
                   205 tgggcaacac gggcctgcaa actcgacagg accctgcccg aggggccctc gcgccaacct        745 ggaccggtcc ccgcctcctc cgctgcccaa tctctcagac ccaccccacc tgcaggccca        805 gaccacgtgg gacagaactc ctgcccaccc taccccgagg gaggcgaacc cgcacttcca        865 ggcttgggag gaccatgggg cacaatgcgg tccagaccct gctgcgtctc ccttccaaac        925 tctggtgctg aataaacccct tctgatctgg tct                                    958
```

<210> SEQ ID NO 4
<211> LENGTH: 206
<212> TYPE: PRT
<213> ORGANISM: Homo sapiens

<400> SEQUENCE: 4

```
Met Gly Ser Gly Pro Arg Gly Ala Leu Ser Leu Leu Leu Leu Leu Leu
1               5                   10                  15

Ala Pro Pro Ser Arg Pro Ala Ala Gly Cys Pro Ala Pro Cys Ser Cys
                20                  25                  30

Ala Gly Thr Leu Val Asp Cys Gly Arg Arg Gly Leu Thr Trp Ala Ser
            35                  40                  45

Leu Pro Thr Ala Phe Pro Val Asp Thr Thr Glu Leu Val Leu Thr Gly
    50                  55                  60

Asn Asn Leu Thr Ala Leu Pro Pro Gly Leu Leu Asp Ala Leu Pro Ala
65                  70                  75                  80

Leu Arg Thr Ala His Leu Gly Ala Asn Pro Trp Arg Cys Asp Cys Arg
                85                  90                  95

Leu Val Pro Leu Arg Ala Trp Leu Ala Gly Arg Pro Glu Arg Ala Pro
                100                 105                 110

Tyr Arg Asp Leu Arg Cys Val Ala Pro Pro Ala Leu Arg Gly Arg Leu
            115                 120                 125

Leu Pro Tyr Leu Ala Glu Asp Glu Leu Arg Ala Ala Cys Ala Pro Gly
    130                 135                 140

Pro Leu Cys Trp Gly Ala Leu Ala Ala Gln Leu Ala Leu Leu Gly Leu
145                 150                 155                 160

Gly Leu Leu His Ala Leu Leu Leu Val Leu Leu Leu Cys Arg Leu Arg
```

```
                      165                 170                 175
Arg Leu Arg Ala Arg Ala Arg Ala Ala Ala Arg Leu Ser Leu
            180                 185                 190

Thr Asp Pro Leu Val Ala Glu Arg Ala Gly Thr Asp Glu Ser
            195                 200                 205

<210> SEQ ID NO 5
<211> LENGTH: 3493
<212> TYPE: DNA
<213> ORGANISM: Homo sapiens
<220> FEATURE:
<221> NAME/KEY: CDS
<222> LOCATION: (32)..(1711)

<400> SEQUENCE: 5
agttactttg gagtgcagaa ccatttcaga c atg ctg agg ggg act cta ctg       52
                                   Met Leu Arg Gly Thr Leu Leu
                                    1               5 tgc gcg gtg ctc ggg ctt ctg cgc gcc cag ccc ttc ccc tgt ccg cca    100
Cys Ala Val Leu Gly Leu Leu Arg Ala Gln Pro Phe Pro Cys Pro Pro
         10                  15                  20 gct tgc aag tgt gtc ttc cgg gac gcc gcg cag tgc tcg ggg ggc gac    148
Ala Cys Lys Cys Val Phe Arg Asp Ala Ala Gln Cys Ser Gly Gly Asp
 25                  30                  35 gtg gcg cgc atc tcc gcg cta ggc ctg ccc acc aac ctc acg cac atc    196
Val Ala Arg Ile Ser Ala Leu Gly Leu Pro Thr Asn Leu Thr His Ile
 40                  45                  50                  55 ctg ctc ttc gga atg ggc cgc ggc gtc ctg cag agc cag agc ttc agc    244
Leu Leu Phe Gly Met Gly Arg Gly Val Leu Gln Ser Gln Ser Phe Ser
                 60                  65                  70 ggc atg acc gtc ctg cag cgc ctc atg atc tcc gac agc cac att tcc    292
Gly Met Thr Val Leu Gln Arg Leu Met Ile Ser Asp Ser His Ile Ser
             75                  80                  85 gcc gtt gcc ccc ggc acc ttc agt gac ctg ata aaa ctg aaa acc ctg    340
Ala Val Ala Pro Gly Thr Phe Ser Asp Leu Ile Lys Leu Lys Thr Leu
         90                  95                 100 agg ctg tcg cgc aac aaa atc acg cat ctt cca ggt gcg ctg ctg gat    388
Arg Leu Ser Arg Asn Lys Ile Thr His Leu Pro Gly Ala Leu Leu Asp
105                 110                 115 aag atg gtg ctc ctg gag cag ttg ttt ttg gac cac aat gcg cta agg    436
Lys Met Val Leu Leu Glu Gln Leu Phe Leu Asp His Asn Ala Leu Arg
120                 125                 130                 135 ggc att gac caa aac atg ttt cag aaa ctg gtt aac ctg cag gag ctc    484
Gly Ile Asp Gln Asn Met Phe Gln Lys Leu Val Asn Leu Gln Glu Leu
                140                 145                 150 gct ctg aac cag aat cag ctc gat ttc ctt cct gcc agt ctc ttc acg    532
Ala Leu Asn Gln Asn Gln Leu Asp Phe Leu Pro Ala Ser Leu Phe Thr
            155                 160                 165 aat ctg gag aac ctg aag ttg ttg gat tta tcg gga aac aac ctg acc    580
Asn Leu Glu Asn Leu Lys Leu Leu Asp Leu Ser Gly Asn Asn Leu Thr
        170                 175                 180 cac ctg ccc aag ggg ttg ctt gga gca cag gct aag ctc gag aga ctt    628
His Leu Pro Lys Gly Leu Leu Gly Ala Gln Ala Lys Leu Glu Arg Leu
    185                 190                 195 ctc ctc cac tcg aac cgc ctt gtg tct ctg gat tcg ggg ctg ttg aac    676
Leu Leu His Ser Asn Arg Leu Val Ser Leu Asp Ser Gly Leu Leu Asn
200                 205                 210                 215 agc ctg ggc gcc ctg acg gag ctg cag ttc cac cga aat cac atc cgt    724
Ser Leu Gly Ala Leu Thr Glu Leu Gln Phe His Arg Asn His Ile Arg
                220                 225                 230
```

-continued

| | | |
|---|---|---|
| tcc atc gca ccc ggg gcc ttc gac cgg ctc cca aac ctc agt tct ttg<br>Ser Ile Ala Pro Gly Ala Phe Asp Arg Leu Pro Asn Leu Ser Ser Leu<br>235                        240                   245 | 772 |
| acg ctt tcg aga aac cac ctt gcg ttt ctc ccc tct gcg ctc ttt ctt<br>Thr Leu Ser Arg Asn His Leu Ala Phe Leu Pro Ser Ala Leu Phe Leu<br>250                       255                    260 | 820 |
| cat tcg cac aat ctg act ctg ttg act ctg ttc gag aac ccg ctg gca<br>His Ser His Asn Leu Thr Leu Leu Thr Leu Phe Glu Asn Pro Leu Ala<br>265                        270                 275 | 868 |
| gag ctc ccg ggg gtg ctc ttc ggg gag atg ggg ggc ctg cag gag ctg<br>Glu Leu Pro Gly Val Leu Phe Gly Glu Met Gly Gly Leu Gln Glu Leu<br>280                       285                  290                295 | 916 |
| tgg ctg aac cgc acc cag ctg cgc acc ctg ccc gcc gcc gcc ttc cgc<br>Trp Leu Asn Arg Thr Gln Leu Arg Thr Leu Pro Ala Ala Ala Phe Arg<br>300                       305                  310 | 964 |
| aac ctg agc cgc ctg cgg tac tta ggg gtg act ctg agc ccg cgg ctg<br>Asn Leu Ser Arg Leu Arg Tyr Leu Gly Val Thr Leu Ser Pro Arg Leu<br>315                       320                   325 | 1012 |
| agc gcg ctt ccg cag ggc gcc ttc cag ggc ctt ggc gag ctc cag gtg<br>Ser Ala Leu Pro Gln Gly Ala Phe Gln Gly Leu Gly Glu Leu Gln Val<br>330                       335                  340 | 1060 |
| ctc gcc ctg cac tcc aac ggc ctg acc gcc ctc ccc gac ggc ttg ctg<br>Leu Ala Leu His Ser Asn Gly Leu Thr Ala Leu Pro Asp Gly Leu Leu<br>345                       350                 355 | 1108 |
| cgc ggc ctc ggc aag ctg cgc cag gtg tcc ctg cgc cgc aac agg ctg<br>Arg Gly Leu Gly Lys Leu Arg Gln Val Ser Leu Arg Arg Asn Arg Leu<br>360                       365                  370                375 | 1156 |
| cgc gcc ctg ccc cgt gcc ctc ttc cgc aat ctc agc agc ctg gag agc<br>Arg Ala Leu Pro Arg Ala Leu Phe Arg Asn Leu Ser Ser Leu Glu Ser<br>                   380                  385                  390 | 1204 |
| gtc cag ctc gac cac aac cag ctg gag acc ctg cct ggc gac gtg ttt<br>Val Gln Leu Asp His Asn Gln Leu Glu Thr Leu Pro Gly Asp Val Phe<br>                   395                  400                  405 | 1252 |
| ggg gct ctg ccc cgg ctg acg gag gtc ctg ttg ggg cac aac tcc tgg<br>Gly Ala Leu Pro Arg Leu Thr Glu Val Leu Leu Gly His Asn Ser Trp<br>410                       415                  420 | 1300 |
| cgc tgc gac tgt ggc ctg ggg ccc ttc ctg ggg tgg ctg cgg cag cac<br>Arg Cys Asp Cys Gly Leu Gly Pro Phe Leu Gly Trp Leu Arg Gln His<br>425                       430                  435 | 1348 |
| cta ggc ctc gtg ggc ggg gaa gag ccc cca cgg tgc gca ggc cct ggg<br>Leu Gly Leu Val Gly Gly Glu Glu Pro Pro Arg Cys Ala Gly Pro Gly<br>440                       445                  450                455 | 1396 |
| gcg cac gcc ggc ctg ccg ctc tgg gcc ctg ccg ggg ggt gac gcg gag<br>Ala His Ala Gly Leu Pro Leu Trp Ala Leu Pro Gly Gly Asp Ala Glu<br>                   460                  465                  470 | 1444 |
| tgc ccg ggc ccc cgg ggc ccg cct ccc cgc ccc gct gcg gac agc tcc<br>Cys Pro Gly Pro Arg Gly Pro Pro Pro Arg Pro Ala Ala Asp Ser Ser<br>475                       480                  485 | 1492 |
| tcg gaa gcc cct gtc cac cca gcc ttg gct ccc aac agc tca gaa ccc<br>Ser Glu Ala Pro Val His Pro Ala Leu Ala Pro Asn Ser Ser Glu Pro<br>490                       495                  500 | 1540 |
| tgg gtg tgg gcc cag ccg gtg acc acg ggc aaa ggt caa gat cat agt<br>Trp Val Trp Ala Gln Pro Val Thr Thr Gly Lys Gly Gln Asp His Ser<br>505                       510                  515 | 1588 |
| ccg ttc tgg ggg ttt tat ttt ctg ctt tta gct gtt cag gcc atg atc<br>Pro Phe Trp Gly Phe Tyr Phe Leu Leu Leu Ala Val Gln Ala Met Ile<br>520                       525                  530                535 | 1636 |
| acc gtg atc atc gtg ttt gct atg att aaa att ggc caa ctc ttt cga<br>Thr Val Ile Ile Val Phe Ala Met Ile Lys Ile Gly Gln Leu Phe Arg<br>540                       545                  550 | 1684 |

```
                                     -continued aaa tta atc aga gag aga gcc ctt ggg taaaccaatg ggaaaatctt         1731
Lys Leu Ile Arg Glu Arg Ala Leu Gly
            555                 560 ctaattactt agaacctgac cagatgtggc tcggagggga atccagaccc gctgctgtct  1791
tgctctccct cccctcccca ctcctcctct cttcttcctc ttctctctca ctgccacgcc  1851
ttcctttccc tcctcctccc cctctccgct ctgtgctctt cattctcaca ggcccgcaac  1911
ccctcctctc tgtgtccccc gcccgttcct ggaaactgag cttgacgttt gtaaactgtg  1971
gttgcctgcc ttccccagct cccacgcggg tgtgcgctga cactgccggg ggcgctggac  2031
tgtgttggac ccatccgtgc tccgctgtgc ctggcttggc gtctggtgga gagagggggcc 2091 tcttcagtgt ctactgagta aggggacagc tccaggccgg ggcctgtctc ctgcacagag  2151
taagccggta atgtttgtg aaatcaatgc gtggataaag gaacacatgc catccaagtg   2211
atgatggctt ttcctggagg gaaaggatag gctgttgctc tatctaattt tttgtttttg  2271
tttttggaca gtctagctct gtggcccagg ctggcgtgca gtgggccgtc tcagttcact  2331
gcagcctccg cctcccaggt tcaagtgatt ctcatgcctc agcgttctga gtagctggga  2391
ttagaggcgt gtgccactac acccggctaa ttttttgtact tttaaagta gagacggggc  2451 tttgccatat tggcctggct gatctcaaac tcctggtctt gaactcctgg ccacaagtga  2511
tctgcccgcc ttggcctccc aaagtgctgg gattacaggc gtaagccact acacctggcc  2571
ctcttcatcg aatttattt gagaagtaga gctcttgcca ttttttccct tgctccattt   2631
ttctcacttt atgtctctct gacctatggg ctacttggga gagcactgga ctccattcat  2691
gcatgagcat tttcaggata agcgacttct gtgaggctga gagaggaaga aaacacggag  2751
ccttccctcc aggtgcccag tgtaggtcca gcgtgtttcc tgagcctcct gtgagtttcc  2811
acttgcttta catccatgca acatgtcatt ttgaaactgg attgatttgc atttcctgga  2871
actctgccac ctcatttcac aagcattat ggagcagtta acatgtgact ggtattcatg   2931
aatataatga taagcttgat tctagttcag ctgctgtcac agtctcattt gttcttccaa  2991
ctgaaagccg taaaacctt gttgctttaa ttgaatgtct gtgcttatga gaggcagtgg   3051
ttaaaacagg ggctggcgag ttgacaactg tgggttcaaa tcccagctct accacttact  3111
aactgcatgg gacttgggt aagacacctg cttacattct ctaagccttg gtttcctgaa   3171
ccttaaaaca ggataacata gtacctgctt cgtagagttt ttgtgagaat taaaggcaat  3231
aaagcatata atgacttagc ccagcggcct gcaggcaata catgttaatg aatgttagct  3291
attattacta aaggatgagc aattattatt ggcatcatga tttctaaaga agagctttga  3351
gttggtattt ttctctgtgt ataagggtaa gtccgaactt tctcagactg gaggttacat  3411
tcacatcagt ctgtcttccc ctgcggatgg cctcagcccc gggtggccag actctgtgct  3471
cacaatccag agcaatggat cc                                          3493

<210> SEQ ID NO 6
<211> LENGTH: 560
<212> TYPE: PRT
<213> ORGANISM: Homo sapiens

<400> SEQUENCE: 6

Met Leu Arg Gly Thr Leu Leu Cys Ala Val Leu Gly Leu Leu Arg Ala
1               5                   10                  15

Gln Pro Phe Pro Cys Pro Pro Ala Cys Lys Cys Val Phe Arg Asp Ala
            20                  25                  30
```

-continued

```
Ala Gln Cys Ser Gly Gly Asp Val Ala Arg Ile Ser Ala Leu Gly Leu
             35                  40                  45

Pro Thr Asn Leu Thr His Ile Leu Leu Phe Gly Met Gly Arg Gly Val
 50                  55                  60

Leu Gln Ser Gln Ser Phe Ser Gly Met Thr Val Leu Gln Arg Leu Met
 65                  70                  75                  80

Ile Ser Asp Ser His Ile Ser Ala Val Ala Pro Gly Thr Phe Ser Asp
                 85                  90                  95

Leu Ile Lys Leu Lys Thr Leu Arg Leu Ser Arg Asn Lys Ile Thr His
             100                 105                 110

Leu Pro Gly Ala Leu Leu Asp Lys Met Val Leu Leu Glu Gln Leu Phe
             115                 120                 125

Leu Asp His Asn Ala Leu Arg Gly Ile Asp Gln Asn Met Phe Gln Lys
         130                 135                 140

Leu Val Asn Leu Gln Glu Leu Ala Leu Asn Gln Asn Gln Leu Asp Phe
145                 150                 155                 160

Leu Pro Ala Ser Leu Phe Thr Asn Leu Glu Asn Leu Lys Leu Leu Asp
                 165                 170                 175

Leu Ser Gly Asn Asn Leu Thr His Leu Pro Lys Gly Leu Leu Gly Ala
             180                 185                 190

Gln Ala Lys Leu Glu Arg Leu Leu Leu His Ser Asn Arg Leu Val Ser
         195                 200                 205

Leu Asp Ser Gly Leu Leu Asn Ser Leu Gly Ala Leu Thr Glu Leu Gln
210                 215                 220

Phe His Arg Asn His Ile Arg Ser Ile Ala Pro Gly Ala Phe Asp Arg
225                 230                 235                 240

Leu Pro Asn Leu Ser Ser Leu Thr Leu Ser Arg Asn His Leu Ala Phe
                 245                 250                 255

Leu Pro Ser Ala Leu Phe Leu His Ser His Asn Leu Thr Leu Leu Thr
             260                 265                 270

Leu Phe Glu Asn Pro Leu Ala Glu Leu Pro Gly Val Leu Phe Gly Glu
         275                 280                 285

Met Gly Gly Leu Gln Glu Leu Trp Leu Asn Arg Thr Gln Leu Arg Thr
290                 295                 300

Leu Pro Ala Ala Ala Phe Arg Asn Leu Ser Arg Leu Arg Tyr Leu Gly
305                 310                 315                 320

Val Thr Leu Ser Pro Arg Leu Ser Ala Leu Pro Gln Gly Ala Phe Gln
                 325                 330                 335

Gly Leu Gly Glu Leu Gln Val Leu Ala Leu His Ser Asn Gly Leu Thr
             340                 345                 350

Ala Leu Pro Asp Gly Leu Leu Arg Gly Leu Gly Lys Leu Arg Gln Val
         355                 360                 365

Ser Leu Arg Arg Asn Arg Leu Arg Ala Leu Pro Arg Ala Leu Phe Arg
370                 375                 380

Asn Leu Ser Ser Leu Glu Ser Val Gln Leu Asp His Asn Gln Leu Glu
385                 390                 395                 400

Thr Leu Pro Gly Asp Val Phe Gly Ala Leu Pro Arg Leu Thr Glu Val
                 405                 410                 415

Leu Leu Gly His Asn Ser Trp Arg Cys Asp Cys Gly Leu Gly Pro Phe
             420                 425                 430

Leu Gly Trp Leu Arg Gln His Leu Gly Leu Val Gly Gly Glu Glu Pro
         435                 440                 445

Pro Arg Cys Ala Gly Pro Gly Ala His Ala Gly Leu Pro Leu Trp Ala
```

```
                450            455             460
Leu Pro Gly Gly Asp Ala Glu Cys Pro Gly Arg Gly Pro Pro
465                 470                 475                 480

Arg Pro Ala Ala Asp Ser Ser Glu Ala Pro Val His Pro Ala Leu
                    485                 490                 495

Ala Pro Asn Ser Ser Glu Pro Trp Val Trp Ala Gln Pro Val Thr Thr
                500                 505                 510

Gly Lys Gly Gln Asp His Ser Pro Phe Trp Gly Phe Tyr Phe Leu Leu
            515                 520                 525

Leu Ala Val Gln Ala Met Ile Thr Val Ile Ile Val Phe Ala Met Ile
            530                 535                 540

Lys Ile Gly Gln Leu Phe Arg Lys Leu Ile Arg Glu Arg Ala Leu Gly
545                 550                 555                 560

<210> SEQ ID NO 7
<211> LENGTH: 900
<212> TYPE: DNA
<213> ORGANISM: Homo sapiens
<220> FEATURE:
<221> NAME/KEY: CDS
<222> LOCATION: (188)..(718)

<400> SEQUENCE: 7
gccaggacct tcaggccag acaggagcac ctgaccaaag gcttcacagc cgccctcacc       60
gcccggcctt ctacggtgtc cagagacagt tagccaggcc tgggctgggc acactccacc      120
ttccctagtc accagctggt ttcccagagg agaaggctga gacccgagaa gggagccagc      180 ctgtccc atg cct gcc tgg gga gcc ctg ttc ctg ctc tgg gcc aca gca      229
        Met Pro Ala Trp Gly Ala Leu Phe Leu Leu Trp Ala Thr Ala
        1               5                   10 gag gcc acc aag gac tgc ccc agc cca tgt acc tgc cgc gcc ctg gaa      277
Glu Ala Thr Lys Asp Cys Pro Ser Pro Cys Thr Cys Arg Ala Leu Glu
15                  20                  25                  30 acc atg ggg ctg tgg gtg gac tgc agg ggc cac gga ctc acg gcc ctg      325
Thr Met Gly Leu Trp Val Asp Cys Arg Gly His Gly Leu Thr Ala Leu
                35                  40                  45 cct gcc ctg ccg gcc cgc acc cgc cac ctt ctg ctg gcc aac aac agc      373
Pro Ala Leu Pro Ala Arg Thr Arg His Leu Leu Leu Ala Asn Asn Ser
            50                  55                  60 ctt cag tcc gtg ccc ccg gga gcc ttt gac cac ctg ccc cag ctg cag      421
Leu Gln Ser Val Pro Pro Gly Ala Phe Asp His Leu Pro Gln Leu Gln
        65                  70                  75 acc ctc gat gtg acg cag aac ccc tgg cac tgt gac tgc agc ctc acc      469
Thr Leu Asp Val Thr Gln Asn Pro Trp His Cys Asp Cys Ser Leu Thr
80                  85                  90 tat ctg cgc ctc tgg ctg gag gac cgc acg ccc gag gcc ctg ctg cag      517
Tyr Leu Arg Leu Trp Leu Glu Asp Arg Thr Pro Glu Ala Leu Leu Gln
95                  100                 105                 110 gtc cgc tgt gcc agc ccc agc ctc gct gcc cat ggc ccg ctg ggc cgg      565
Val Arg Cys Ala Ser Pro Ser Leu Ala Ala His Gly Pro Leu Gly Arg
                115                 120                 125 ctg aca ggc tac cag ctg ggc agc tgt ggc tgg cag ctg cag gcg tcc      613
Leu Thr Gly Tyr Gln Leu Gly Ser Cys Gly Trp Gln Leu Gln Ala Ser
            130                 135                 140 tgg gtg cgc ccg ggg gtc ttg tgg gac gtg gcg ctg gtc gcc gtg gcc      661
Trp Val Arg Pro Gly Val Leu Trp Asp Val Ala Leu Val Ala Val Ala
        145                 150                 155 gcg ctg ggc ctg gct ctt ctg gct ggc ctg ctg tgt gcc acc aca gag      709
Ala Leu Gly Leu Ala Leu Leu Ala Gly Leu Leu Cys Ala Thr Thr Glu
```

```
                   160                 165                 170
gcc ctg gat tgagccaggc ccccagaacc cctggctcca ggccagggg              758
Ala Leu Asp
175 ccagtccctg aggcaggtcc ccagactcca ccaagcctgg tcagcccaaa ccaccagaag   818 cccagaataa actggcagct cagctgtttt atataaaaaa aaaaaaaaaa aaaaaaaaaa   878 aaaaaaaaaa aaaaaaaaaa aa                                           900
```

<210> SEQ ID NO 8
<211> LENGTH: 177
<212> TYPE: PRT
<213> ORGANISM: Homo sapiens

<400> SEQUENCE: 8

```
Met Pro Ala Trp Gly Ala Leu Phe Leu Leu Trp Ala Thr Ala Glu Ala
1               5                   10                  15

Thr Lys Asp Cys Pro Ser Pro Cys Thr Cys Arg Ala Leu Glu Thr Met
            20                  25                  30

Gly Leu Trp Val Asp Cys Arg Gly His Gly Leu Thr Ala Leu Pro Ala
        35                  40                  45

Leu Pro Ala Arg Thr Arg His Leu Leu Leu Ala Asn Asn Ser Leu Gln
    50                  55                  60

Ser Val Pro Pro Gly Ala Phe Asp His Leu Pro Gln Leu Gln Thr Leu
65                  70                  75                  80

Asp Val Thr Gln Asn Pro Trp His Cys Asp Cys Ser Leu Thr Tyr Leu
                85                  90                  95

Arg Leu Trp Leu Glu Asp Arg Thr Pro Glu Ala Leu Leu Gln Val Arg
            100                 105                 110

Cys Ala Ser Pro Ser Leu Ala Ala His Gly Pro Leu Gly Arg Leu Thr
        115                 120                 125

Gly Tyr Gln Leu Gly Ser Cys Gly Trp Gln Leu Gln Ala Ser Trp Val
    130                 135                 140

Arg Pro Gly Val Leu Trp Asp Val Ala Leu Val Ala Val Ala Ala Leu
145                 150                 155                 160

Gly Leu Ala Leu Leu Ala Gly Leu Leu Cys Ala Thr Thr Glu Ala Leu
                165                 170                 175

Asp
```

<210> SEQ ID NO 9
<211> LENGTH: 8833
<212> TYPE: DNA
<213> ORGANISM: Homo sapiens
<220> FEATURE:
<221> NAME/KEY: CDS
<222> LOCATION: (251)..(8689)

<400> SEQUENCE: 9

```
agctcacagc tattgtggtg ggaaagggag ggtggttggt ggatgtcaca gcttgggctt    60
tatctccccc agcagtgggg actccacagc ccctgggcta cataacagca agacagtccg   120
gagctgtagc agacctgatt gagcctttgc agcagctgag agcatggcct agggtgggcg   180
gcaccattgt ccagcagctg agtttcccag ggaccttgga gatagccgca gccctcattt   240
gcaggggaag atg att cct gcc aga ttt gcc ggg gtg ctg ctt gct ctg    289
            Met Ile Pro Ala Arg Phe Ala Gly Val Leu Leu Ala Leu
            1               5                   10 gcc ctc att ttg cca ggg acc ctt tgt gca gaa gga act cgc ggc agg    337
```

|   |   |   |   |   |   |   |   |   |   |   |   |
|---|---|---|---|---|---|---|---|---|---|---|---|
| Ala | Leu | Ile | Leu | Pro | Gly | Thr | Leu | Cys | Ala | Glu | Gly | Thr | Arg | Gly | Arg |
|  | 15 |  |  |  | 20 |  |  |  | 25 |  |  |  |  |  |  |

```
tca tcc acg gcc cga tgc agc ctt ttc gga agt gac ttc gtc aac acc        385
Ser Ser Thr Ala Arg Cys Ser Leu Phe Gly Ser Asp Phe Val Asn Thr
30              35                  40                  45 ttt gat ggg agc atg tac agc ttt gcg gga tac tgc agt tac ctc ctg        433
Phe Asp Gly Ser Met Tyr Ser Phe Ala Gly Tyr Cys Ser Tyr Leu Leu
                50                  55                  60 gca ggg ggc tgc cag aaa cgc tcc ttc tcg att att ggg gac ttc cag        481
Ala Gly Gly Cys Gln Lys Arg Ser Phe Ser Ile Ile Gly Asp Phe Gln
            65                  70                  75 aat ggc aag aga gtg agc ctc tcc gtg tat ctt ggg gaa ttt ttt gac        529
Asn Gly Lys Arg Val Ser Leu Ser Val Tyr Leu Gly Glu Phe Phe Asp
        80                  85                  90 atc cat ttg ttt gtc aat ggt acc gtg aca cag ggg gac caa aga gtc        577
Ile His Leu Phe Val Asn Gly Thr Val Thr Gln Gly Asp Gln Arg Val
    95                  100                 105 tcc atg ccc tat gcc tcc aaa ggg ctg tat cta gaa act gag gct ggg        625
Ser Met Pro Tyr Ala Ser Lys Gly Leu Tyr Leu Glu Thr Glu Ala Gly
110                 115                 120                 125 tac tac aag ctg tcc ggt gag gcc tat ggc ttt gtg gcc agg atc gat        673
Tyr Tyr Lys Leu Ser Gly Glu Ala Tyr Gly Phe Val Ala Arg Ile Asp
                130                 135                 140 ggc agc ggc aac ttt caa gtc ctg ctg tca gac aga tac ttc aac aag        721
Gly Ser Gly Asn Phe Gln Val Leu Leu Ser Asp Arg Tyr Phe Asn Lys
            145                 150                 155 acc tgc ggg ctg tgt ggc aac ttt aac atc ttt gct gaa gat gac ttt        769
Thr Cys Gly Leu Cys Gly Asn Phe Asn Ile Phe Ala Glu Asp Asp Phe
        160                 165                 170 atg acc caa gaa ggg acc ttg acc tcg gac cct tat gac ttt gcc aac        817
Met Thr Gln Glu Gly Thr Leu Thr Ser Asp Pro Tyr Asp Phe Ala Asn
    175                 180                 185 tca tgg gct ctg agc agt gga gaa cag tgg tgt gaa cgg gca tct cct        865
Ser Trp Ala Leu Ser Ser Gly Glu Gln Trp Cys Glu Arg Ala Ser Pro
190                 195                 200                 205 ccc agc agc tca tgc aac atc tcc tct ggg gaa atg cag aag ggc ctg        913
Pro Ser Ser Ser Cys Asn Ile Ser Ser Gly Glu Met Gln Lys Gly Leu
                210                 215                 220 tgg gag cag tgc cag ctt ctg aag agc acc tcg gtg ttt gcc cgc tgc        961
Trp Glu Gln Cys Gln Leu Leu Lys Ser Thr Ser Val Phe Ala Arg Cys
            225                 230                 235 cac cct ctg gtg gac ccc gag cct ttt gtg gcc ctg tgt gag aag act       1009
His Pro Leu Val Asp Pro Glu Pro Phe Val Ala Leu Cys Glu Lys Thr
        240                 245                 250 ttg tgt gag tgt gct ggg ggg ctg gag tgc gcc tgc cct gcc ctc ctg       1057
Leu Cys Glu Cys Ala Gly Gly Leu Glu Cys Ala Cys Pro Ala Leu Leu
    255                 260                 265 gag tac gcc cgg acc tgt gcc cag gag gga atg gtg ctg tac ggc tgg       1105
Glu Tyr Ala Arg Thr Cys Ala Gln Glu Gly Met Val Leu Tyr Gly Trp
270                 275                 280                 285 acc gac cac agc gcg tgc agc cca gtg tgc cct gct ggt atg gag tat       1153
Thr Asp His Ser Ala Cys Ser Pro Val Cys Pro Ala Gly Met Glu Tyr
                290                 295                 300 agg cag tgt gtg tcc cct tgc gcc agg acc tgc cag agc ctg cac atc       1201
Arg Gln Cys Val Ser Pro Cys Ala Arg Thr Cys Gln Ser Leu His Ile
            305                 310                 315 aat gaa atg tgt cag gag cga tgc gtg gat ggc tgc agc tgc cct gag       1249
Asn Glu Met Cys Gln Glu Arg Cys Val Asp Gly Cys Ser Cys Pro Glu
        320                 325                 330
```

| | | |
|---|---|---|
| gga cag ctc ctg gat gaa ggc ctc tgc gtg gag agc acc gag tgt ccc<br>Gly Gln Leu Leu Asp Glu Gly Leu Cys Val Glu Ser Thr Glu Cys Pro<br>335         340             345 | | 1297 |
| tgc gtg cat tcc gga aag cgc tac cct ccc ggc acc tcc ctc tct cga<br>Cys Val His Ser Gly Lys Arg Tyr Pro Pro Gly Thr Ser Leu Ser Arg<br>350         355             360             365 | | 1345 |
| gac tgc aac acc tgc att tgc cga aac agc cag tgg atc tgc agc aat<br>Asp Cys Asn Thr Cys Ile Cys Arg Asn Ser Gln Trp Ile Cys Ser Asn<br>                370             375             380 | | 1393 |
| gaa gaa tgt cca ggg gag tgc ctt gtc aca ggt caa tca cac ttc aag<br>Glu Glu Cys Pro Gly Glu Cys Leu Val Thr Gly Gln Ser His Phe Lys<br>            385             390             395 | | 1441 |
| agc ttt gac aac aga tac ttc acc ttc agt ggg atc tgc cag tac ctg<br>Ser Phe Asp Asn Arg Tyr Phe Thr Phe Ser Gly Ile Cys Gln Tyr Leu<br>        400             405             410 | | 1489 |
| ctg gcc cgg gat tgc cag gac cac tcc ttc tcc att gtc att gag act<br>Leu Ala Arg Asp Cys Gln Asp His Ser Phe Ser Ile Val Ile Glu Thr<br>    415             420             425 | | 1537 |
| gtc cag tgt gct gat gac cgc gac gct gtg tgc acc cgc tcc gtc acc<br>Val Gln Cys Ala Asp Asp Arg Asp Ala Val Cys Thr Arg Ser Val Thr<br>430             435             440             445 | | 1585 |
| gtc cgg ctg cct ggc ctg cac aac agc ctt gtg aaa ctg aag cat ggg<br>Val Arg Leu Pro Gly Leu His Asn Ser Leu Val Lys Leu Lys His Gly<br>                450             455             460 | | 1633 |
| gca gga gtt gcc atg gat ggc cag gac gtc cag ctc ccc ctc ctg aaa<br>Ala Gly Val Ala Met Asp Gly Gln Asp Val Gln Leu Pro Leu Leu Lys<br>            465             470             475 | | 1681 |
| ggt gac ctc cgc atc cag cat aca gtg acg gcc tcc gtg cgc ctc agc<br>Gly Asp Leu Arg Ile Gln His Thr Val Thr Ala Ser Val Arg Leu Ser<br>        480             485             490 | | 1729 |
| tac ggg gag gac ctg cag atg gac tgg gat ggc cgc ggg agg ctg ctg<br>Tyr Gly Glu Asp Leu Gln Met Asp Trp Asp Gly Arg Gly Arg Leu Leu<br>    495             500             505 | | 1777 |
| gtg aag ctg tcc ccc gtc tat gcc ggg aag acc tgc ggc ctg tgt ggg<br>Val Lys Leu Ser Pro Val Tyr Ala Gly Lys Thr Cys Gly Leu Cys Gly<br>510             515             520             525 | | 1825 |
| aat tac aat ggc aac cag ggc gac gac ttc ctt acc ccc tct ggg ctg<br>Asn Tyr Asn Gly Asn Gln Gly Asp Asp Phe Leu Thr Pro Ser Gly Leu<br>                530             535             540 | | 1873 |
| gcg gag ccc cgg gtg gag gac ttc ggg aac gcc tgg aag ctg cac ggg<br>Ala Glu Pro Arg Val Glu Asp Phe Gly Asn Ala Trp Lys Leu His Gly<br>            545             550             555 | | 1921 |
| gac tgc cag gac ctg cag aag cag cac agc gat ccc tgc gcc ctc aac<br>Asp Cys Gln Asp Leu Gln Lys Gln His Ser Asp Pro Cys Ala Leu Asn<br>        560             565             570 | | 1969 |
| ccg cgc atg acc agg ttc tcc gag gag gcg tgc gcg gtc ctg acg tcc<br>Pro Arg Met Thr Arg Phe Ser Glu Glu Ala Cys Ala Val Leu Thr Ser<br>    575             580             585 | | 2017 |
| ccc aca ttc gag gcc tgc cat cgt gcc gtc agc ccg ctg ccc tac ctg<br>Pro Thr Phe Glu Ala Cys His Arg Ala Val Ser Pro Leu Pro Tyr Leu<br>590             595             600             605 | | 2065 |
| cgg aac tgc cgc tac gac gtg tgc tcc tgc tcg gac ggc cgc gag tgc<br>Arg Asn Cys Arg Tyr Asp Val Cys Ser Cys Ser Asp Gly Arg Glu Cys<br>                610             615             620 | | 2113 |
| ctg tgc ggc gcc ctg gcc agc tat gcc gcg gcc tgc gcg ggg aga ggc<br>Leu Cys Gly Ala Leu Ala Ser Tyr Ala Ala Ala Cys Ala Gly Arg Gly<br>            625             630             635 | | 2161 |
| gtg cgc gtc gcg tgg cgc gag cca ggc cgc tgt gag ctg aac tgc ccg<br>Val Arg Val Ala Trp Arg Glu Pro Gly Arg Cys Glu Leu Asn Cys Pro<br>        640             645             650 | | 2209 |

| | | |
|---|---|---|
| aaa ggc cag gtg tac ctg cag tgc ggg acc ccc tgc aac ctg acc tgc<br>Lys Gly Gln Val Tyr Leu Gln Cys Gly Thr Pro Cys Asn Leu Thr Cys<br>655 660 665 | | 2257 |
| cgc tct ctc tct tac ccg gat gag gaa tgc aat gag gcc tgc ctg gag<br>Arg Ser Leu Ser Tyr Pro Asp Glu Glu Cys Asn Glu Ala Cys Leu Glu<br>670 675 680 685 | | 2305 |
| ggc tgc ttc tgc ccc cca ggg ctc tac atg gat gag agg ggg gac tgc<br>Gly Cys Phe Cys Pro Pro Gly Leu Tyr Met Asp Glu Arg Gly Asp Cys<br>690 695 700 | | 2353 |
| gtg ccc aag gcc cag tgc ccc tgt tac tat gac ggt gag atc ttc cag<br>Val Pro Lys Ala Gln Cys Pro Cys Tyr Tyr Asp Gly Glu Ile Phe Gln<br>705 710 715 | | 2401 |
| cca gaa gac atc ttc tca gac cat cac acc atg tgc tac tgt gag gat<br>Pro Glu Asp Ile Phe Ser Asp His His Thr Met Cys Tyr Cys Glu Asp<br>720 725 730 | | 2449 |
| ggc ttc atg cac tgt acc atg agt gga gtc ccc gga agc ttg ctg cct<br>Gly Phe Met His Cys Thr Met Ser Gly Val Pro Gly Ser Leu Leu Pro<br>735 740 745 | | 2497 |
| gac gct gtc ctc agc agt ccc ctg tct cat cgc agc aaa agg agc cta<br>Asp Ala Val Leu Ser Ser Pro Leu Ser His Arg Ser Lys Arg Ser Leu<br>750 755 760 765 | | 2545 |
| tcc tgt cgg ccc ccc atg gtc aag ctg gtg tgt ccc gct gac aac ctg<br>Ser Cys Arg Pro Pro Met Val Lys Leu Val Cys Pro Ala Asp Asn Leu<br>770 775 780 | | 2593 |
| cgg gct gaa ggg ctc gag tgt acc aaa acg tgc cag aac tat gac ctg<br>Arg Ala Glu Gly Leu Glu Cys Thr Lys Thr Cys Gln Asn Tyr Asp Leu<br>785 790 795 | | 2641 |
| gag tgc atg agc atg ggc tgt gtc tct ggc tgc ctc tgc ccc ccg ggc<br>Glu Cys Met Ser Met Gly Cys Val Ser Gly Cys Leu Cys Pro Pro Gly<br>800 805 810 | | 2689 |
| atg gtc cgg cat gag aac aga tgt gtg gcc ctg gaa agg tgt ccc tgc<br>Met Val Arg His Glu Asn Arg Cys Val Ala Leu Glu Arg Cys Pro Cys<br>815 820 825 | | 2737 |
| ttc cat cag ggc aag gag tat gcc cct gga gaa aca gtg aag att ggc<br>Phe His Gln Gly Lys Glu Tyr Ala Pro Gly Glu Thr Val Lys Ile Gly<br>830 835 840 845 | | 2785 |
| tgc aac act tgt gtc tgt cgg gac cgg aag tgg aac tgc aca gac cat<br>Cys Asn Thr Cys Val Cys Arg Asp Arg Lys Trp Asn Cys Thr Asp His<br>850 855 860 | | 2833 |
| gtg tgt gat gcc acg tgc tcc acg atc ggc atg gcc cac tac ctc acc<br>Val Cys Asp Ala Thr Cys Ser Thr Ile Gly Met Ala His Tyr Leu Thr<br>865 870 875 | | 2881 |
| ttc gac ggg ctc aaa tac ctg ttc ccc ggg gag tgc cag tac gtt ctg<br>Phe Asp Gly Leu Lys Tyr Leu Phe Pro Gly Glu Cys Gln Tyr Val Leu<br>880 885 890 | | 2929 |
| gtg cag gat tac tgc ggc agt aac cct ggg acc ttt cgg atc cta gtg<br>Val Gln Asp Tyr Cys Gly Ser Asn Pro Gly Thr Phe Arg Ile Leu Val<br>895 900 905 | | 2977 |
| ggg aat aag gga tgc agc cac ccc tca gtg aaa tgc aag aaa cgg gtc<br>Gly Asn Lys Gly Cys Ser His Pro Ser Val Lys Cys Lys Lys Arg Val<br>910 915 920 925 | | 3025 |
| acc atc ctg gtg gag gga gga gag att gag ctg ttt gac ggg gag gtg<br>Thr Ile Leu Val Glu Gly Gly Glu Ile Glu Leu Phe Asp Gly Glu Val<br>930 935 940 | | 3073 |
| aat gtg aag agg ccc atg aag gat gag act cac ttt gag gtg gtg gag<br>Asn Val Lys Arg Pro Met Lys Asp Glu Thr His Phe Glu Val Val Glu<br>945 950 955 | | 3121 |
| tct ggc cgg tac atc att ctg ctg ctg ggc aaa gcc ctc tcc gtg gtc<br>Ser Gly Arg Tyr Ile Ile Leu Leu Leu Gly Lys Ala Leu Ser Val Val | | 3169 |

-continued

```
              960                 965                 970
tgg gac cgc cac ctg agc atc tcc gtg gtc ctg aag cag aca tac cag    3217
Trp Asp Arg His Leu Ser Ile Ser Val Val Leu Lys Gln Thr Tyr Gln
    975                 980                 985 gag aaa gtg tgt ggc ctg tgt ggg aat ttt gat ggc atc cag aac aat    3265
Glu Lys Val Cys Gly Leu Cys Gly Asn Phe Asp Gly Ile Gln Asn Asn
990                 995                 1000                1005 gac ctc acc agc agc  aac ctc caa gtg gag  gaa gac cct gtg gac      3310
Asp Leu Thr Ser Ser  Asn Leu Gln Val Glu  Glu Asp Pro Val Asp
                1010                1015                1020 ttt ggg aac tcc tgg  aaa gtg agc tcg cag  tgt gct gac acc aga      3355
Phe Gly Asn Ser Trp  Lys Val Ser Ser Gln  Cys Ala Asp Thr Arg
                1025                1030                1035 aaa gtg cct ctg gac  tca tcc cct gcc acc  tgc cat aac aac atc      3400
Lys Val Pro Leu Asp  Ser Ser Pro Ala Thr  Cys His Asn Asn Ile
                1040                1045                1050 atg aag cag acg atg  gtg gat tcc tcc tgt  aga atc ctt acc agt      3445
Met Lys Gln Thr Met  Val Asp Ser Ser Cys  Arg Ile Leu Thr Ser
                1055                1060                1065 gac gtc ttc cag gac  tgc aac aag ctg gtg  gac ccc gag cca tat      3490
Asp Val Phe Gln Asp  Cys Asn Lys Leu Val  Asp Pro Glu Pro Tyr
                1070                1075                1080 ctg gat gtc tgc att  tac gac acc tgc tcc  tgt gag tcc att ggg      3535
Leu Asp Val Cys Ile  Tyr Asp Thr Cys Ser  Cys Glu Ser Ile Gly
                1085                1090                1095 gac tgc gcc tgc ttc  tgc gac acc att gct  gcc tat gcc cac gtg      3580
Asp Cys Ala Cys Phe  Cys Asp Thr Ile Ala  Ala Tyr Ala His Val
                1100                1105                1110 tgt gcc cag cat ggc  aag gtg gtg acc tgg  agg acg gcc aca ttg      3625
Cys Ala Gln His Gly  Lys Val Val Thr Trp  Arg Thr Ala Thr Leu
                1115                1120                1125 tgc ccc cag agc tgc  gag gag agg aat ctc  cgg gag aac ggg tat      3670
Cys Pro Gln Ser Cys  Glu Glu Arg Asn Leu  Arg Glu Asn Gly Tyr
                1130                1135                1140 gag tgt gag tgg cgc  tat aac agc tgt gca  cct gcc tgt caa gtc      3715
Glu Cys Glu Trp Arg  Tyr Asn Ser Cys Ala  Pro Ala Cys Gln Val
                1145                1150                1155 acg tgt cag cac cct  gag cca ctg gcc tgc  cct gtg cag tgt gtg      3760
Thr Cys Gln His Pro  Glu Pro Leu Ala Cys  Pro Val Gln Cys Val
                1160                1165                1170 gag ggc tgc cat gcc  cac tgc cct cca ggg  aaa atc ctg gat gag      3805
Glu Gly Cys His Ala  His Cys Pro Pro Gly  Lys Ile Leu Asp Glu
                1175                1180                1185 ctt ttg cag acc tgc  gtt gac cct gaa gac  tgt cca gtg tgt gag      3850
Leu Leu Gln Thr Cys  Val Asp Pro Glu Asp  Cys Pro Val Cys Glu
                1190                1195                1200 gtg gct ggc cgg cgt  ttt gcc tca gga aag  aaa gtc acc ttg aat      3895
Val Ala Gly Arg Arg  Phe Ala Ser Gly Lys  Lys Val Thr Leu Asn
                1205                1210                1215 ccc agt gac cct gag  cac tgc cag att tgc  cac tgt gat gtt gtc      3940
Pro Ser Asp Pro Glu  His Cys Gln Ile Cys  His Cys Asp Val Val
                1220                1225                1230 aac ctc acc tgt gaa  gcc tgc cag gag ccg  gga ggc ctg gtg gtg      3985
Asn Leu Thr Cys Glu  Ala Cys Gln Glu Pro  Gly Gly Leu Val Val
                1235                1240                1245 cct ccc aca gat gcc  ccg gtg agc ccc acc  act ctg tat gtg gag      4030
Pro Pro Thr Asp Ala  Pro Val Ser Pro Thr  Thr Leu Tyr Val Glu
                1250                1255                1260 gac atc tcg gaa ccg  ccg ttg cac gat ttc  tac tgc agc agg cta      4075
Asp Ile Ser Glu Pro  Pro Leu His Asp Phe  Tyr Cys Ser Arg Leu
```

```
                Asp Ile Ser Glu Pro Pro Leu His Asp Phe Tyr Cys Ser Arg Leu
                              1265                1270                1275 ctg gac ctg gtc ttc ctg ctg gat ggc tcc tcc agg ctg tcc gag              4120
Leu Asp Leu Val Phe Leu Leu Asp Gly Ser Ser Arg Leu Ser Glu
            1280                1285                1290 gct gag ttt gaa gtg ctg aag gcc ttt gtg gtg gac atg atg gag              4165
Ala Glu Phe Glu Val Leu Lys Ala Phe Val Val Asp Met Met Glu
            1295                1300                1305 cgg ctg cgc atc tcc cag aag tgg gtc cgc gtg gcc gtg gtg gag              4210
Arg Leu Arg Ile Ser Gln Lys Trp Val Arg Val Ala Val Val Glu
            1310                1315                1320 tac cac gac ggc tcc cac gcc tac atc ggg ctc aag gac cgg aag              4255
Tyr His Asp Gly Ser His Ala Tyr Ile Gly Leu Lys Asp Arg Lys
            1325                1330                1335 cga ccg tca gag ctg cgg cgc att gcc agc cag gtg aag tat gcg              4300
Arg Pro Ser Glu Leu Arg Arg Ile Ala Ser Gln Val Lys Tyr Ala
            1340                1345                1350 ggc agc cag gtg gcc tcc acc agc gag gtc ttg aaa tac aca ctg              4345
Gly Ser Gln Val Ala Ser Thr Ser Glu Val Leu Lys Tyr Thr Leu
            1355                1360                1365 ttc caa atc ttc agc aag atc gac cgc cct gaa gcc tcc cgc atc              4390
Phe Gln Ile Phe Ser Lys Ile Asp Arg Pro Glu Ala Ser Arg Ile
            1370                1375                1380 acc ctg ctc ctg atg gcc agc cag gag ccc caa cgg atg tcc cgg              4435
Thr Leu Leu Leu Met Ala Ser Gln Glu Pro Gln Arg Met Ser Arg
            1385                1390                1395 aac ttt gtc cgc tac gtc cag ggc ctg aag aag aag aag gtc att              4480
Asn Phe Val Arg Tyr Val Gln Gly Leu Lys Lys Lys Lys Val Ile
            1400                1405                1410 gtg atc ccg gtg ggc att ggg ccc cat gcc aac ctc aag cag atc              4525
Val Ile Pro Val Gly Ile Gly Pro His Ala Asn Leu Lys Gln Ile
            1415                1420                1425 cgc ctc atc gag aag cag gcc cct gag aac aag gcc ttc gtg ctg              4570
Arg Leu Ile Glu Lys Gln Ala Pro Glu Asn Lys Ala Phe Val Leu
            1430                1435                1440 agc agt gtg gat gag ctg gag cag caa agg gac gag atc gtt agc              4615
Ser Ser Val Asp Glu Leu Glu Gln Gln Arg Asp Glu Ile Val Ser
            1445                1450                1455 tac ctc tgt gac ctt gcc cct gaa gcc cct cct cct act ctg ccc              4660
Tyr Leu Cys Asp Leu Ala Pro Glu Ala Pro Pro Pro Thr Leu Pro
            1460                1465                1470 ccc gac atg gca caa gtc act gtg ggc ccg ggg ctc ttg ggg gtt              4705
Pro Asp Met Ala Gln Val Thr Val Gly Pro Gly Leu Leu Gly Val
            1475                1480                1485 tcg acc ctg ggg ccc aag agg aac tcc atg gtt ctg gat gtg gcg              4750
Ser Thr Leu Gly Pro Lys Arg Asn Ser Met Val Leu Asp Val Ala
            1490                1495                1500 ttc gtc ctg gaa gga tcg gac aaa att ggt gaa gcc gac ttc aac              4795
Phe Val Leu Glu Gly Ser Asp Lys Ile Gly Glu Ala Asp Phe Asn
            1505                1510                1515 agg agc aag gag ttc atg gag gag gtg att cag cgg atg gat gtg              4840
Arg Ser Lys Glu Phe Met Glu Glu Val Ile Gln Arg Met Asp Val
            1520                1525                1530 ggc cag gac agc atc cac gtc acg gtg ctg cag tac tcc tac atg              4885
Gly Gln Asp Ser Ile His Val Thr Val Leu Gln Tyr Ser Tyr Met
            1535                1540                1545 gtg act gtg gag tac ccc ttc agc gag gca cag tcc aaa ggg gac              4930
Val Thr Val Glu Tyr Pro Phe Ser Glu Ala Gln Ser Lys Gly Asp
            1550                1555                1560
```

```
atc ctg cag cgg gtg cga gag atc cgc tac cag ggc ggc aac agg      4975
Ile Leu Gln Arg Val Arg Glu Ile Arg Tyr Gln Gly Gly Asn Arg
                1565                1570                1575 acc aac act ggg ctg gcc ctg cgg tac ctc tct gac cac agc ttc      5020
Thr Asn Thr Gly Leu Ala Leu Arg Tyr Leu Ser Asp His Ser Phe
        1580                1585                1590 ttg gtc agc cag ggt gac cgg gag cag gcg ccc aac ctg gtc tac      5065
Leu Val Ser Gln Gly Asp Arg Glu Gln Ala Pro Asn Leu Val Tyr
    1595                1600                1605 atg gtc acc gga aat cct gcc tct gat gag atc aag agg ctg cct      5110
Met Val Thr Gly Asn Pro Ala Ser Asp Glu Ile Lys Arg Leu Pro
1610                1615                1620 gga gac atc cag gtg gtg ccc att gga gtg ggc cct aat gcc aac      5155
Gly Asp Ile Gln Val Val Pro Ile Gly Val Gly Pro Asn Ala Asn
                1625                1630                1635 gtg cag gag ctg gag agg att ggc tgg ccc aat gcc cct atc ctc      5200
Val Gln Glu Leu Glu Arg Ile Gly Trp Pro Asn Ala Pro Ile Leu
        1640                1645                1650 atc cag gac ttt gag acg ctc ccc cga gag gct cct gac ctg gtg      5245
Ile Gln Asp Phe Glu Thr Leu Pro Arg Glu Ala Pro Asp Leu Val
    1655                1660                1665 ctg cag agg tgc tgc tcc gga gag ggg ctg cag atc ccc acc ctc      5290
Leu Gln Arg Cys Cys Ser Gly Glu Gly Leu Gln Ile Pro Thr Leu
1670                1675                1680 tcc cct gca cct gac tgc agc cag ccc ctg gac gtg atc ctt ctc      5335
Ser Pro Ala Pro Asp Cys Ser Gln Pro Leu Asp Val Ile Leu Leu
                1685                1690                1695 ctg gat ggc tcc tcc agt ttc cca gct tct tat ttt gat gaa atg      5380
Leu Asp Gly Ser Ser Ser Phe Pro Ala Ser Tyr Phe Asp Glu Met
        1700                1705                1710 aag agt ttc gcc aag gct ttc att tca aaa gcc aat ata ggg cct      5425
Lys Ser Phe Ala Lys Ala Phe Ile Ser Lys Ala Asn Ile Gly Pro
    1715                1720                1725 cgt ctc act cag gtg tca gtg ctg cag tat gga agc atc acc acc      5470
Arg Leu Thr Gln Val Ser Val Leu Gln Tyr Gly Ser Ile Thr Thr
1730                1735                1740 att gac gtg cca tgg aac gtg gtc ccg gag aaa gcc cat ttg ctg      5515
Ile Asp Val Pro Trp Asn Val Val Pro Glu Lys Ala His Leu Leu
                1745                1750                1755 agc ctt gtg gac gtc atg cag cgg gag gga ggc ccc agc caa atc      5560
Ser Leu Val Asp Val Met Gln Arg Glu Gly Gly Pro Ser Gln Ile
        1760                1765                1770 ggg gat gcc ttg ggc ttt gct gtg cga tac ttg act tca gaa atg      5605
Gly Asp Ala Leu Gly Phe Ala Val Arg Tyr Leu Thr Ser Glu Met
    1775                1780                1785 cat ggt gcc agg ccg gga gcc tca aag gcg gtg gtc atc ctg gtc      5650
His Gly Ala Arg Pro Gly Ala Ser Lys Ala Val Val Ile Leu Val
1790                1795                1800 acg gac gtc tct gtg gat tca gtg gat gca gca gct gat gcc gcc      5695
Thr Asp Val Ser Val Asp Ser Val Asp Ala Ala Ala Asp Ala Ala
                1805                1810                1815 agg tcc aac aga gtg aca gtg ttc cct att gga att gga gat cgc      5740
Arg Ser Asn Arg Val Thr Val Phe Pro Ile Gly Ile Gly Asp Arg
        1820                1825                1830 tac gat gca gcc cag cta cgg atc ttg gca ggc cca gca ggc gac      5785
Tyr Asp Ala Ala Gln Leu Arg Ile Leu Ala Gly Pro Ala Gly Asp
    1835                1840                1845 tcc aac gtg gtg aag ctc cag cga atc gaa gac ctc cct acc atg      5830
Ser Asn Val Val Lys Leu Gln Arg Ile Glu Asp Leu Pro Thr Met
1850                1855                1860
```

-continued

```
gtc acc ttg ggc aat tcc ttc ctc cac aaa ctg tgc tct gga ttt         5875
Val Thr Leu Gly Asn Ser Phe Leu His Lys Leu Cys Ser Gly Phe
            1865                1870                1875 gtt agg att tgc atg gat gag gat ggg aat gag aag agg ccc ggg         5920
Val Arg Ile Cys Met Asp Glu Asp Gly Asn Glu Lys Arg Pro Gly
            1880                1885                1890 gac gtc tgg acc ttg cca gac cag tgc cac acc gtg act tgc cag         5965
Asp Val Trp Thr Leu Pro Asp Gln Cys His Thr Val Thr Cys Gln
            1895                1900                1905 cca gat ggc cag acc ttg ctg aag agt cat cgg gtc aac tgt gac         6010
Pro Asp Gly Gln Thr Leu Leu Lys Ser His Arg Val Asn Cys Asp
            1910                1915                1920 cgg ggg ctg agg cct tcg tgc cct aac agc cag tcc cct gtt aaa         6055
Arg Gly Leu Arg Pro Ser Cys Pro Asn Ser Gln Ser Pro Val Lys
            1925                1930                1935 gtg gaa gag acc tgt ggc tgc cgc tgg acc tgc ccc tgc gtg tgc         6100
Val Glu Glu Thr Cys Gly Cys Arg Trp Thr Cys Pro Cys Val Cys
            1940                1945                1950 aca ggc agc tcc act cgg cac atc gtg acc ttt gat ggg cag aat         6145
Thr Gly Ser Ser Thr Arg His Ile Val Thr Phe Asp Gly Gln Asn
            1955                1960                1965 ttc aag ctg act ggc agc tgt tct tat gtc cta ttt caa aac aag         6190
Phe Lys Leu Thr Gly Ser Cys Ser Tyr Val Leu Phe Gln Asn Lys
            1970                1975                1980 gag cag gac ctg gag gtg att ctc cat aat ggt gcc tgc agc cct         6235
Glu Gln Asp Leu Glu Val Ile Leu His Asn Gly Ala Cys Ser Pro
            1985                1990                1995 gga gca agg cag ggc tgc atg aaa tcc atc gag gtg aag cac agt         6280
Gly Ala Arg Gln Gly Cys Met Lys Ser Ile Glu Val Lys His Ser
            2000                2005                2010 gcc ctc tcc gtc gag ctg cac agt gac atg gag gtg acg gtg aat         6325
Ala Leu Ser Val Glu Leu His Ser Asp Met Glu Val Thr Val Asn
            2015                2020                2025 ggg aga ctg gtc tct gtt cct tac gtg ggt ggg aac atg gaa gtc         6370
Gly Arg Leu Val Ser Val Pro Tyr Val Gly Gly Asn Met Glu Val
            2030                2035                2040 aac gtt tat ggt gcc atc atg cat gag gtc aga ttc aat cac ctt         6415
Asn Val Tyr Gly Ala Ile Met His Glu Val Arg Phe Asn His Leu
            2045                2050                2055 ggt cac atc ttc aca ttc act cca caa aac aat gag ttc caa ctg         6460
Gly His Ile Phe Thr Phe Thr Pro Gln Asn Asn Glu Phe Gln Leu
            2060                2065                2070 cag ctc agc ccc aag act ttt gct tca aag acg tat ggt ctg tgt         6505
Gln Leu Ser Pro Lys Thr Phe Ala Ser Lys Thr Tyr Gly Leu Cys
            2075                2080                2085 ggg atc tgt gat gag aac gga gcc aat gac ttc atg ctg agg gat         6550
Gly Ile Cys Asp Glu Asn Gly Ala Asn Asp Phe Met Leu Arg Asp
            2090                2095                2100 ggc aca gtc acc aca gac tgg aaa aca ctt gtt cag gaa tgg act         6595
Gly Thr Val Thr Thr Asp Trp Lys Thr Leu Val Gln Glu Trp Thr
            2105                2110                2115 gtg cag cgg cca ggg cag acg tgc cag ccc atc ctg gag gag cag         6640
Val Gln Arg Pro Gly Gln Thr Cys Gln Pro Ile Leu Glu Glu Gln
            2120                2125                2130 tgt ctt gtc ccc gac agc tcc cac tgc cag gtc ctc ctc tta cca         6685
Cys Leu Val Pro Asp Ser Ser His Cys Gln Val Leu Leu Leu Pro
            2135                2140                2145 ctg ttt gct gaa tgc cac aag gtc ctg gct cca gcc aca ttc tat         6730
Leu Phe Ala Glu Cys His Lys Val Leu Ala Pro Ala Thr Phe Tyr
```

-continued

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     |     |     | 2150|     |     |     |     | 2155|     |     |     | 2160|      |
| gcc | atc | tgc | cag | cag | gac | agt | tgc | cac | cag | gag | caa | gtg | tgt | gag | 6775 |
| Ala | Ile | Cys | Gln | Gln | Asp | Ser | Cys | His | Gln | Glu | Gln | Val | Cys | Glu |      |
|     |     |     |     | 2165|     |     |     |     | 2170|     |     |     |     | 2175|      |
| gtg | atc | gcc | tct | tat | gcc | cac | ctc | tgt | cgg | acc | aac | ggg | gtc | tgc | 6820 |
| Val | Ile | Ala | Ser | Tyr | Ala | His | Leu | Cys | Arg | Thr | Asn | Gly | Val | Cys |      |
|     |     |     |     | 2180|     |     |     |     | 2185|     |     |     |     | 2190|      |
| gtt | gac | tgg | agg | aca | cct | gat | ttc | tgt | gct | atg | tca | tgc | cca | cca | 6865 |
| Val | Asp | Trp | Arg | Thr | Pro | Asp | Phe | Cys | Ala | Met | Ser | Cys | Pro | Pro |      |
|     |     |     |     | 2195|     |     |     |     | 2200|     |     |     |     | 2205|      |
| tct | ctg | gtc | tac | aac | cac | tgt | gag | cat | ggc | tgt | ccc | cgg | cac | tgt | 6910 |
| Ser | Leu | Val | Tyr | Asn | His | Cys | Glu | His | Gly | Cys | Pro | Arg | His | Cys |      |
|     |     |     |     | 2210|     |     |     |     | 2215|     |     |     |     | 2220|      |
| gat | ggc | aac | gtg | agc | tcc | tgt | ggg | gac | cat | ccc | tcc | gaa | ggc | tgt | 6955 |
| Asp | Gly | Asn | Val | Ser | Ser | Cys | Gly | Asp | His | Pro | Ser | Glu | Gly | Cys |      |
|     |     |     |     | 2225|     |     |     |     | 2230|     |     |     |     | 2235|      |
| ttc | tgc | cct | cca | gat | aaa | gtc | atg | ttg | gaa | ggc | agc | tgt | gtc | cct | 7000 |
| Phe | Cys | Pro | Pro | Asp | Lys | Val | Met | Leu | Glu | Gly | Ser | Cys | Val | Pro |      |
|     |     |     |     | 2240|     |     |     |     | 2245|     |     |     |     | 2250|      |
| gaa | gag | gcc | tgc | act | cag | tgc | att | ggt | gag | gat | gga | gtc | cag | cac | 7045 |
| Glu | Glu | Ala | Cys | Thr | Gln | Cys | Ile | Gly | Glu | Asp | Gly | Val | Gln | His |      |
|     |     |     |     | 2255|     |     |     |     | 2260|     |     |     |     | 2265|      |
| cag | ttc | ctg | gaa | gcc | tgg | gtc | ccg | gac | cac | cag | ccc | tgt | cag | atc | 7090 |
| Gln | Phe | Leu | Glu | Ala | Trp | Val | Pro | Asp | His | Gln | Pro | Cys | Gln | Ile |      |
|     |     |     |     | 2270|     |     |     |     | 2275|     |     |     |     | 2280|      |
| tgc | aca | tgc | ctc | agc | ggg | cgg | aag | gtc | aac | tgc | aca | acg | cag | ccc | 7135 |
| Cys | Thr | Cys | Leu | Ser | Gly | Arg | Lys | Val | Asn | Cys | Thr | Thr | Gln | Pro |      |
|     |     |     |     | 2285|     |     |     |     | 2290|     |     |     |     | 2295|      |
| tgc | ccc | acg | gcc | aaa | gct | ccc | acg | tgt | ggc | ctg | tgt | gaa | gta | gcc | 7180 |
| Cys | Pro | Thr | Ala | Lys | Ala | Pro | Thr | Cys | Gly | Leu | Cys | Glu | Val | Ala |      |
|     |     |     |     | 2300|     |     |     |     | 2305|     |     |     |     | 2310|      |
| cgc | ctc | cgc | cag | aat | gca | gac | cag | tgc | tgc | ccc | gag | tat | gag | tgt | 7225 |
| Arg | Leu | Arg | Gln | Asn | Ala | Asp | Gln | Cys | Cys | Pro | Glu | Tyr | Glu | Cys |      |
|     |     |     |     | 2315|     |     |     |     | 2320|     |     |     |     | 2325|      |
| gtg | tgt | gac | cca | gtg | agc | tgt | gac | ctg | ccc | cca | gtg | cct | cac | tgt | 7270 |
| Val | Cys | Asp | Pro | Val | Ser | Cys | Asp | Leu | Pro | Pro | Val | Pro | His | Cys |      |
|     |     |     |     | 2330|     |     |     |     | 2335|     |     |     |     | 2340|      |
| gaa | cgt | ggc | ctc | cag | ccc | aca | ctg | acc | aac | cct | ggc | gag | tgc | aga | 7315 |
| Glu | Arg | Gly | Leu | Gln | Pro | Thr | Leu | Thr | Asn | Pro | Gly | Glu | Cys | Arg |      |
|     |     |     |     | 2345|     |     |     |     | 2350|     |     |     |     | 2355|      |
| ccc | aac | ttc | acc | tgc | gcc | tgc | agg | aag | gag | gag | tgc | aaa | aga | gtg | 7360 |
| Pro | Asn | Phe | Thr | Cys | Ala | Cys | Arg | Lys | Glu | Glu | Cys | Lys | Arg | Val |      |
|     |     |     |     | 2360|     |     |     |     | 2365|     |     |     |     | 2370|      |
| tcc | cca | ccc | tcc | tgc | ccc | ccg | cac | cgt | ttg | ccc | acc | ctt | cgg | aag | 7405 |
| Ser | Pro | Pro | Ser | Cys | Pro | Pro | His | Arg | Leu | Pro | Thr | Leu | Arg | Lys |      |
|     |     |     |     | 2375|     |     |     |     | 2380|     |     |     |     | 2385|      |
| acc | cag | tgc | tgt | gat | gag | tat | gag | tgt | gcc | tgc | aac | tgt | gtc | aac | 7450 |
| Thr | Gln | Cys | Cys | Asp | Glu | Tyr | Glu | Cys | Ala | Cys | Asn | Cys | Val | Asn |      |
|     |     |     |     | 2390|     |     |     |     | 2395|     |     |     |     | 2400|      |
| tcc | aca | gtg | agc | tgt | ccc | ctt | ggg | tac | ttg | gcc | tca | act | gcc | acc | 7495 |
| Ser | Thr | Val | Ser | Cys | Pro | Leu | Gly | Tyr | Leu | Ala | Ser | Thr | Ala | Thr |      |
|     |     |     |     | 2405|     |     |     |     | 2410|     |     |     |     | 2415|      |
| aat | gac | tgt | ggc | tgt | acc | aca | acc | acc | tgc | ctt | ccc | gac | aag | gtg | 7540 |
| Asn | Asp | Cys | Gly | Cys | Thr | Thr | Thr | Thr | Cys | Leu | Pro | Asp | Lys | Val |      |
|     |     |     |     | 2420|     |     |     |     | 2425|     |     |     |     | 2430|      |
| tgt | gtc | cac | cga | agc | acc | atc | tac | cct | gtg | ggc | cag | ttc | tgg | gag | 7585 |
| Cys | Val | His | Arg | Ser | Thr | Ile | Tyr | Pro | Val | Gly | Gln | Phe | Trp | Glu |      |
|     |     |     |     | 2435|     |     |     |     | 2440|     |     |     |     | 2445|      |
| gag | ggc | tgc | gat | gtg | tgc | acc | tgc | acc | gac | atg | gag | gat | gcc | gtg | 7630 |

| | | | | | | | | | | |
|---|---|---|---|---|---|---|---|---|---|---|
|Glu|Gly|Cys|Asp|Val|Cys|Thr|Cys|Thr|Asp|Met|Glu|Asp|Ala|Val|
| | | |2450| | |2455| | | |2460|

```
atg ggc ctc cgc gtg gcc cag tgc tcc cag aag ccc tgt gag gac    7675
Met Gly Leu Arg Val Ala Gln Cys Ser Gln Lys Pro Cys Glu Asp
            2465                2470                2475 agc tgt cgg tcg ggc ttc act tac gtt ctg cat gaa ggc gag tgc    7720
Ser Cys Arg Ser Gly Phe Thr Tyr Val Leu His Glu Gly Glu Cys
            2480                2485                2490 tgt gga agg tgc ctg cca tct gcc tgt gag gtg gtg act ggc tca    7765
Cys Gly Arg Cys Leu Pro Ser Ala Cys Glu Val Val Thr Gly Ser
            2495                2500                2505 ccg cgg ggg gac tcc cag tct tcc tgg aag agt gtc ggc tcc cag    7810
Pro Arg Gly Asp Ser Gln Ser Ser Trp Lys Ser Val Gly Ser Gln
            2510                2515                2520 tgg gcc tcc ccg gag aac ccc tgc ctc atc aat gag tgt gtc cga    7855
Trp Ala Ser Pro Glu Asn Pro Cys Leu Ile Asn Glu Cys Val Arg
            2525                2530                2535 gtg aag gag gag gtc ttt ata caa caa agg aac gtc tcc tgc ccc    7900
Val Lys Glu Glu Val Phe Ile Gln Gln Arg Asn Val Ser Cys Pro
            2540                2545                2550 cag ctg gag gtc cct gtc tgc ccc tcg ggc ttt cag ctg agc tgt    7945
Gln Leu Glu Val Pro Val Cys Pro Ser Gly Phe Gln Leu Ser Cys
            2555                2560                2565 aag acc tca gcg tgc tgc cca agc tgt cgc tgt gag cgc atg gag    7990
Lys Thr Ser Ala Cys Cys Pro Ser Cys Arg Cys Glu Arg Met Glu
            2570                2575                2580 gcc tgc atg ctc aat ggc act gtc att ggg ccc ggg aag act gtg    8035
Ala Cys Met Leu Asn Gly Thr Val Ile Gly Pro Gly Lys Thr Val
            2585                2590                2595 atg atc gat gtg tgc acg acc tgc cgc tgc atg gtg cag gtg ggg    8080
Met Ile Asp Val Cys Thr Thr Cys Arg Cys Met Val Gln Val Gly
            2600                2605                2610 gtc atc tct gga ttc aag ctg gag tgc agg aag acc acc tgc aac    8125
Val Ile Ser Gly Phe Lys Leu Glu Cys Arg Lys Thr Thr Cys Asn
            2615                2620                2625 ccc tgc ccc ctg ggt tac aag gaa gaa aat aac aca ggt gaa tgt    8170
Pro Cys Pro Leu Gly Tyr Lys Glu Glu Asn Asn Thr Gly Glu Cys
            2630                2635                2640 tgt ggg aga tgt ttg cct acg gct tgc acc att cag cta aga gga    8215
Cys Gly Arg Cys Leu Pro Thr Ala Cys Thr Ile Gln Leu Arg Gly
            2645                2650                2655 gga cag atc atg aca ctg aag cgt gat gag acg ctc cag gat ggc    8260
Gly Gln Ile Met Thr Leu Lys Arg Asp Glu Thr Leu Gln Asp Gly
            2660                2665                2670 tgt gat act cac ttc tgc aag gtc aat gag aga gga gag tac ttc    8305
Cys Asp Thr His Phe Cys Lys Val Asn Glu Arg Gly Glu Tyr Phe
            2675                2680                2685 tgg gag aag agg gtc aca ggc tgc cca ccc ttt gat gaa cac aag    8350
Trp Glu Lys Arg Val Thr Gly Cys Pro Pro Phe Asp Glu His Lys
            2690                2695                2700 tgt ctg gct gag gga ggt aaa att atg aaa att cca ggc acc tgc    8395
Cys Leu Ala Glu Gly Gly Lys Ile Met Lys Ile Pro Gly Thr Cys
            2705                2710                2715 tgt gac aca tgt gag gag cct gag tgc aac gac atc act gcc agg    8440
Cys Asp Thr Cys Glu Glu Pro Glu Cys Asn Asp Ile Thr Ala Arg
            2720                2725                2730 ctg cag tat gtc aag gtg gga agc tgt aag tct gaa gta gag gtg    8485
Leu Gln Tyr Val Lys Val Gly Ser Cys Lys Ser Glu Val Glu Val
            2735                2740                2745
```

```
gat atc cac tac tgc cag ggc aaa tgt gcc agc aaa gcc atg tac        8530
Asp Ile His Tyr Cys Gln Gly Lys Cys Ala Ser Lys Ala Met Tyr
                2750                2755            2760 tcc att gac atc aac gat gtg cag gac cag tgc tcc tgc tgc tct        8575
Ser Ile Asp Ile Asn Asp Val Gln Asp Gln Cys Ser Cys Cys Ser
                2765                2770            2775 ccg aca cgg acg gag ccc atg cag gtg gcc ctg cac tgc acc aat        8620
Pro Thr Arg Thr Glu Pro Met Gln Val Ala Leu His Cys Thr Asn
                2780                2785            2790 ggc tct gtt gtg tac cat gag gtt ctc aat gcc atg gag tgc aaa        8665
Gly Ser Val Val Tyr His Glu Val Leu Asn Ala Met Glu Cys Lys
                2795                2800            2805 tgc tcc ccc agg aag tgc agc aag tgaggctgct gcagctgcat gggtgcctgc   8719
Cys Ser Pro Arg Lys Cys Ser Lys
                2810 tgctgcctgc cttggcctga tggccaggcc agagtgctgc cagtcctctg catgttctgc  8779 tcttgtgccc ttctgagccc acaataaagg ctgagctctt atcttgcaaa aggc        8833
```

METHODS AND KITS FOR MEASURING VON WILLEBRAND FACTOR

CROSS-REFERENCE TO RELATED APPLICATIONS

This application is a continuation of U.S. application Ser. No. 13/153,105, filed Jun. 3, 2011, which is a continuation of U.S. application Ser. No. 12/197,057, filed Aug. 22, 2008, which claims the benefit of U.S. Provisional Patent Application No. 60/957,604, filed Aug. 23, 2007, each incorporated herein by reference as if set forth in its entirety.

STATEMENT REGARDING FEDERALLY SPONSORED RESEARCH

This invention was made with United States government support under grant numbers RO1-HL033721-19 and RO1-HL081588-03, awarded by the National Institutes of Health. The United States government has certain rights in this invention.

BACKGROUND

The invention relates generally to methods and kits for measuring von Willebrand factor (VWF), and more particularly to methods and kits for measuring VWF that do not require a platelet agglutination agonist, such as ristocetin.

VWF is a multimeric glycoprotein synthesized by megakaryocytes and endothelial cells, which is subsequently secreted into blood plasma as a spectrum of multimers. VWF binds other proteins, especially proteins involved in hemostasis, such as Factor VIII (an essential clotting factor that participates in the intrinsic pathway of blood coagulation) and platelet glycoprotein Ib (GPIb; a component of a platelet adhesion receptor complex). VWF is deficient or defective in von Willebrand disease (VWD) and is involved in a large number of other diseases, including thrombotic thrombocytopenic purpura, Heyde's syndrome and possibly hemolytic-uremic syndrome. See, Sadler J, "Biochemistry and genetics of von Willebrand factor". Annu Rev. Biochem. 67:395-424 (1998). VWF levels can be affected by many factors including ABO blood group and ethnicity.

VWD is a common bleeding disorder characterized by either qualitative or quantitative defects in tests for VWF. Symptoms of VWD include easy bruising, menorrhagia and epistaxis. Currently, many types of hereditary VWD are known (e.g., type 1; type 2A, 2B, 2M, 2N and type 3, as well as platelet-type, pseudo VWD, which results from a defect in platelet GPIb); however, acquired forms of VWD are also known, but are less frequently observed. Of particular interest herein is platelet-type, pseudo VWD. In contrast to the other forms of VWD, the genetic defect in platelet-type, pseudo VWD is in platelets rather than VWF and is characterized by abnormally high binding affinity of an individual's platelets to VWF, leading to a characteristic platelet hyper-responsiveness in vitro to a low concentration of ristocetin.

Additional screening tests for VWD include those that measure Factor VIII activity, VWF antigen (VWF:Ag), VWF binding to collagen (VWF:CB) and VWF ristocetin cofactor activity (VWF:RCo). Of particular interest herein is VWF:RCo, which is presently the standard for measurement of VWF function. VWF:RCo utilizes an ability of VWF to bind platelet GPIb following activation by ristocetin, which results in a VWF-dependent agglutination of platelets that can be measured quantitatively by platelet aggregometry or turbidometry. See, Macfarlane D, et al., "A method for assaying von Willebrand factor (ristocetin cofactor)," Thromb. Diath. Haemorrh. 34:306-308 (1975). In fact, an international reference standard for VWF:RCo was assigned a biologic activity in international units by the World Health Organization (WHO) and the Scientific and Standardization Committee of the International Society on Thrombosis and Haemostasis (ISTH).

Unfortunately, VWF:RCo, has several shortcomings. For one, VWF:RCo has high intra- and inter-assay imprecision because of its dependence on ristocetin. See, e.g., Chng W, et al., "Differential effect of the ABO blood group on von Willebrand factor collagen binding activity and ristocetin cofactor assay," Blood Coagul. Fibrinolysis 16:75-78 (2005); Favaloro E, "An update on the von Willebrand factor collagen binding assay: 21 years of age and beyond adolescence but not yet a mature adult," Semin. Thromb. Hemost. 33:727-744 (2007); and Riddel A, et al., "Use of the collagen-binding assay for von Willebrand factor in the analysis of type 2M von Willebrand disease: a comparison with the ristocetin cofactor assay," Br. J. Haematol. 116:187-192 (2002). Federici et at recently described an alternative assay with improved reproducibility that used recombinant GPIb in an enzyme-linked immunosorbant assay of VWF binding; however, it is ristocetin dependent. See, Federici A, et al., "A sensitive ristocetin co-factor activity assay with recombinant glycoprotein Ib for diagnosis of patients with low von Willebrand factor levels," Haematologica 89:77-85 (2004).

In addition, VWF:RCo does not always reflect the true in vivo function of VWF when mutations or polymorphisms are in the ristocetin-binding region of VWF. For example, some individuals have VWF mutations that show a reduced interaction with ristocetin such that VWF:RCo is markedly reduced (e.g., <0.12 IU/dL), although they have no bleeding symptoms even with a major surgical challenge. See, Flood V, et al., "Common VWF haplotypes in normal African-Americans and Caucasians recruited into the ZPMCB-VWD and their impact on VWF laboratory testing," Blood 10:Abstract 714 (2007); Mackie I, et al., "Ristocetin-induced platelet agglutination in Afro-Caribbean and Caucasian people," Br. J. Haematol. 50:171-173 (1982); and Miller C, et al., "Measurement of von Willebrand factor activity: relative effects of ABO blood type and race," J. Thromb. Haemost. 1:2191-2197 (2003). These individuals, who appear to have a polymorphism in the ristocetin-binding region, do not have an abnormality in the binding of VWF to platelet GPIb.

Furthermore, VWF:RCo is affected by high-affinity VWF/platelet disorders. For example, individuals with platelet-type, pseudo VWD have GPIb mutations that cause spontaneous binding of their platelets to VWF. See, Franchini M, et al., "Clinical, laboratory and therapeutic aspects of platelet-type von Willebrand disease," Int. J. Lab. Hematol. 30:91-94 (2008); Miller J & Castella A, "Platelet-type von Willebrand's disease: characterization of a new bleeding disorder," Blood 60:790-794 (1982); and Miller J, "Platelet-type von Willebrand's Disease," Thromb. Haemost. 75:865-869 (1996). Likewise, individuals with type 2B VWD have VWF mutations that cause spontaneous binding to platelets. See, Weiss H, "Type 2B von Willebrand disease and related disorders of patients with increased ristocetin-induced platelet aggregation: what they tell us about the role of von Willebrand factor in hemostasis," J. Thromb. Haemost. 2:2055-2056 (2004).

Because of the wide variability and reproducibility of VWF:RCo, the art desires a VWF function assay that does not require a platelet aggregation agonist, such as ristocetin (i.e., ristocetinless).

BRIEF SUMMARY

The invention relates generally to methods and kits for measuring VWF without requiring a platelet agglutination agonist by utilizing recombinant platelet GPIb gain-of-function mutations. As used herein, a "platelet agglutination agonist" means an agent that facilitates adhesion between VWF and GPIb in platelet agglutination tests. Examples of platelet agglutination agonist include, but are not limited to, ristocetin and botrocetin.

In a first aspect, the present invention is summarized as a method of measuring VWF without requiring a platelet agglutination agonist by providing a surface with immobilized recombinant platelet GPIbα having at least two mutations selected from G233V, D235Y and M239V relative to SEQ ID NO:2 or a functional fragment thereof. The method also includes contacting a sample having or suspected of having VWF with the immobilized GPIbα or functional fragment thereof without using the platelet agglutination agonist. The method also includes detecting a complex, if any, of VWF and the immobilized GPIbα or functional fragment thereof.

In some embodiments of the first aspect, the surface can be a cell surface such that the method is a flow cytometry (FC) or fluorescence-activated cell sorting (FACS) assay. Suitable host cells can be a *Xenopus* oocyte, CHO-K1 cell, L929 cell, HEK-293T cell, COS-7 cell or S2 cell engineered to comprise a polynucleotide encoding platelet GPIbα having the at least two mutations selected from the group consisting of G233V, D235Y and M239V relative to SEQ ID NO:2 or a functional fragment thereof. The host cell also can be engineered to further comprise a polynucleotide encoding platelet glycoprotein Ibβ (GPIbβ; SEQ ID NO:4) and/or optionally platelet glycoprotein IX (GP-IX; SEQ ID NO:8) or functional fragments thereof.

In some embodiments of the first aspect, the surface can be a solid-phase surface such that the method is an enzyme-linked immunosorbant assay (ELISA). The solid-phase surface can be agarose, glass, latex or plastic.

In some embodiments of the first aspect, the complex can be detected with a labeled anti-VWF antibody or functional fragment thereof, such as a fluorescently labeled antibody or fluorescently labeled functional fragment thereof. Alternatively, the complex can be detected by surface plasmon resonance or quasi-elastic light scattering.

In some embodiments of the first aspect, the sample can be a biological sample from an individual having or suspected of having VWD, such as plasma.

In some embodiments of the first aspect, the at least two mutations can be D235Y/G233V, D235Y/M239V or G233V/M239V. In other embodiments of the first aspect, the at least two mutation can be a triple mutation, such as D235Y/G233V/M239V.

In a second aspect, the present invention is summarized as a kit for measuring VWF that includes recombinant platelet GPIbα having at least two mutations selected from G233V, D235Y and M239V relative to SEQ ID NO:2 or a functional fragment thereof. The kit also includes a reagent to detect a complex of VWF and GPIbα.

In some embodiments of the second aspect, the reagent can be a labeled anti-VWF antibody or labeled functional fragment thereof, such as a fluorescently labeled antibody or fluorescently labeled functional fragment thereof.

In some embodiments of the second aspect, the kit further includes a negative or positive control or both. If included, the negative control can be VWF-depleted plasma. If included, the positive control can be pooled plasma from individuals that do not have VWD or can be a commercially available standard, such as those available from WHO and ISTH. In other embodiments of the second aspect, the kit further includes an abnormal control. If included, the abnormal control can be pooled plasma from individuals with variant forms of VWD, such as type-2A, 2B or 2M VWD, as well as pooled plasma from individuals with true loss of in vivo VWF function or pooled plasma individuals that are not appropriately assayed using VWF:RCo (i.e., plasma from individuals having any gain-of-function mutation in VWF).

In some embodiments of the second aspect, the at least two mutations can be selected from D235Y/G233V, D235Y/M239V or G233V/M239V. In other embodiments of the second aspect, the at least two mutations can be a triple mutation, such as D235Y/G233V/M239V.

In some embodiments of the second aspect, the recombinant platelet GPIbα having at least two mutations selected from G233V, D235Y and M239V relative to SEQ ID NO:2 or functional fragment thereof can be immobilized to a surface. In certain embodiments, the surface can be a host cell surface of a host cell that does not natively express platelet GPIbα, as described above. In certain other embodiments, the surface can be a solid-phase surface, as described above.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 2A, y-axis is mean fluorescence and x-axis is log ristocetin concentration in mg/ml), ristocetin (FIG. 2B, y-axis is mean fluorescence and x-axis is log ristocetin concentration in mg/ml) and botrocetin (FIG. 2C, y-axis is mean fluorescence and x-axis is log botrocetin concentration in mg/ml) during FACS. Mock is a HEK-293T cells transfected with an empty expression vector.

Figure 1:
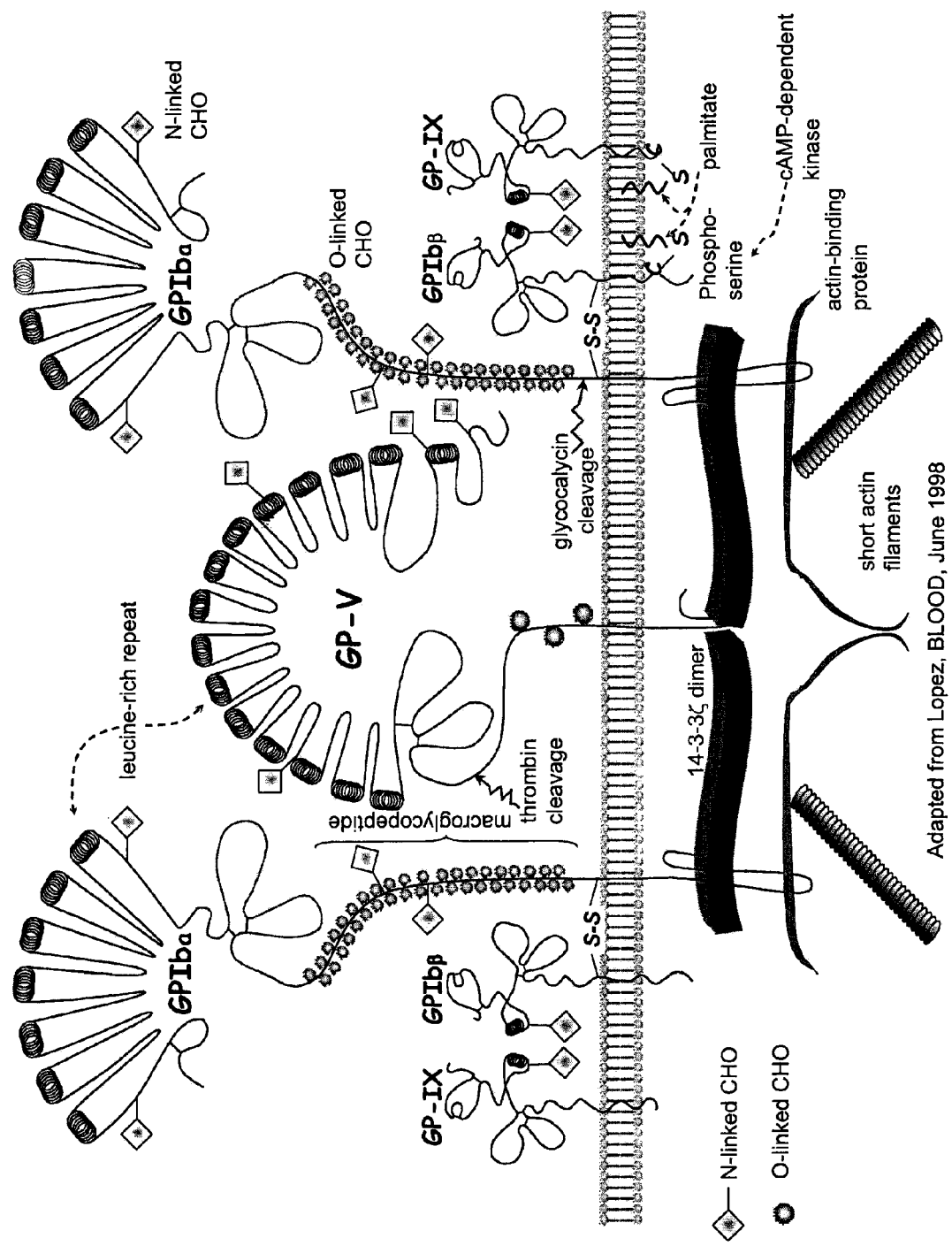
FIG. 1 is a schematic illustration of the platelet adhesion receptor, which shows the components of the receptor, including GPIbα, GPIbβ, GP-V and GP-IX.

While the present invention is susceptible to various modifications and alternative forms, exemplary embodiments thereof are shown by way of example in the drawings and are herein described in detail. It should be understood, however, that the description of preferred embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF PREFERRED EMBODIMENTS

The present invention stems from the inventor's observation that some individuals with VWD have VWF mutations that lower VWF:RCo (i.e., <10 IU/dL), even though their in vivo VWF function is normal (i.e., VWF still binds to the platelet adhesion receptor component GPIb). See, Friedman K, et al., "Factitious diagnosis of type 2M von Willebrand disease (VWD) with a mutation in von Willebrand factor (VWF) that affects the ristocetin cofactor assay but does not significantly affect VWF function in vitro," Blood 98:536a (2001).

In contrast, other individuals with VWD (i.e., type 2B and platelet-type VWD) have VWF or GPIbα mutations that lower the concentration of ristocetin required for platelet aggregation in an assay for VWF function. This paradox results from gain-of-function mutations that cause VWF multimers and the GPIb receptors on platelets to bind more tightly to one another. The inventor hypothesized that recombinant gain-of-function GPIbα mutations could be useful in assays for VWF function, thereby avoiding ristocetin (i.e., ristocetinless). As used herein, "ristocetinless" or "agonistless" means that ristocetin or other platelet agglutination agonists (i.e., botrocetin) are not required in a VWF assay.

The present invention therefore broadly relates to novel methods and kits for VWF utilizing gain-of-function GPIbα mutations, especially GPIbα mutations identified in individuals having platelet-type, pseudo VWD, to measure VWF (herein called "VWF:IbCo"). The methods and kits are useful in a variety of applications. For example, the methods and kits disclosed herein may be used for diagnosing VWD in an individual suspected of having VWD, classifying VWD in an individual diagnosed with VWD and monitoring treatment in an individual having VWD.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

As used herein, "about" means within 5% of a stated concentration range, purity range, temperature range or stated time frame.

As used herein, a "coding sequence" means a sequence that encodes a particular polypeptide, such as GPIbα, and is a nucleic acid sequence that is transcribed (in the case of DNA) and translated (in the case of mRNA) into that polypeptide in vitro or in vivo when placed under the control of appropriate regulatory sequences. The boundaries of the coding sequence are determined by a start codon at a 5' (amino) terminus and a translation stop codon at a 3' (carboxy) terminus. A coding sequence can include, but is not limited to, viral nucleic acid sequences, cDNA from prokaryotic or eukaryotic mRNA, genomic DNA sequences from prokaryotic or eukaryotic DNA, and even synthetic DNA sequences. A transcription termination sequence will usually be located 3' to the coding sequence.

As used herein, an "expression sequence" means a control sequence operably linked to a coding sequence.

As used herein, "control sequences" means promoter sequences, polyadenylation signals, transcription termination sequences, upstream regulatory domains, origins of replication, internal ribosome entry sites ("IRES"), enhancers, and the like, which collectively provide for replication, transcription and translation of a coding sequence in a recipient cell. Not all of these control sequences need always be present so long as the selected coding sequence is capable of being replicated, transcribed and translated in an appropriate host cell.

As used herein, a "promoter" means a nucleotide region comprising a nucleic acid (i.e., DNA) regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is repressed by an analyte, cofactor, regulatory protein, etc.) and "constitutive promoters" (where expression of a polynucleotide sequence operably linked to the promoter is unregulated and therefore continuous).

As used herein, a "nucleic acid" sequence means a DNA or RNA sequence. The term encompasses sequences that include, but are not limited to, any of the known base analogues of DNA and RNA such as 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine and 2,6-diaminopurine.

As used herein, "operably linked" means that elements of an expression sequence are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. For example, intervening untranslated, yet transcribed, sequences can be present between a promoter and a coding sequence, and the promoter sequence can still be considered "operably linked" to the coding sequence.

As used herein, "operable interaction" means that subunits of a polypeptide (e.g., the components of the platelet adhesion receptor, such as GPIbβ and/or GP-IX), and any other accessory proteins, that are heterologously expressed in a host cell assemble into a functioning platelet adhesion receptor (i.e., capable of binding with VWF or functional fragments thereof capable of binding VWF).

As used herein, a "vector" means a replicon, such as a plasmid, phage or cosmid, to which another nucleic acid segment may be attached so as to bring about the replication of the attached segment. A vector is capable of transferring gene sequences to target cells (e.g., bacterial plasmid vectors, particulate carriers and liposomes).

Typically, the terms "vector construct," "expression vector," "gene expression vector," "gene delivery vector," "gene transfer vector" and "expression cassette" all refer to an assembly that is capable of directing the expression of a coding sequence or gene of interest. Thus, the terms include cloning and expression vehicles.

As used herein, an "isolated polynucleotide" or "isolated polypeptide" means a polynucleotide or polypeptide isolated from its natural environment or prepared using synthetic methods such as those known to one of ordinary skill in the art. Complete purification is not required in either case. The polynucleotides and polypeptides described herein can be isolated and purified from normally associated material in conventional ways, such that in the purified preparation the polynucleotide or polypeptide is the predominant species in the preparation. At the very least, the degree of purification is such that extraneous material in the preparation does not interfere with use of the polynucleotide or polypeptide in the manner disclosed herein. The polynucleotide or polypeptide is at least about 85% pure; alternatively, at least about 95% pure; and alternatively, at least about 99% pure.

Further, an isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

As used herein, "homologous" means those polynucleotides or polypeptides sharing at least about 90% or at least about 95% sequence identity to, e.g., SEQ ID NOS:1-6, respectively, that result in functional polypeptides that bind VWF. For example, a polypeptide that is at least about 90% or at least about 95% identical to the GPIbα mutations discussed herein is expected to be a constituent of the platelet adhesion receptor. One of ordinary skill in the art understands that modifications to either the polynucleotide or the polypeptide includes substitutions, insertions (e.g., adding no more than about ten nucleotides or amino acids) and deletions (e.g., deleting no more than about ten nucleotides or amino acids). These modifications can be introduced into the polynucleotide or polypeptide described below without abolishing structure and ultimately, function. Polynucleotides and/or polypeptides containing such modifications can be used in the methods of the present invention. Such polypeptides can be identified by using the screening methods described below.

An isolated nucleic acid containing a polynucleotide (or its complement) that can hybridize to any of the uninterrupted nucleic acid sequences described above, under either stringent or moderately stringent hybridization conditions, is also within the scope of the present invention. Stringent hybridization conditions are defined as hybridizing at 68° C. in 5×SSC/5×Denhardt's solution/1.0% SDS, and washing in 0.2×SSC/0.1% SDS+/−100 µg/ml denatured salmon sperm DNA at room temperature, and moderately stringent hybridization conditions are defined as washing in the same buffer at 42° C. Additional guidance regarding such conditions is readily available in the art, e.g., in Sambrook J, et al. (eds.), "Molecular cloning: a laboratory manual," (3rd ed. Cold Spring Harbor Press, Cold Spring Harbor, N.Y. 2001); and Ausubel F, et al. (eds.), "Current Protocols in Molecular Biology," (John Wiley & Sons, N.Y. 1995), each of which is incorporated herein by reference as if set forth in its entirety.

It is well known in the art that amino acids within the same conservative group can typically substitute for one another without substantially affecting the function of a protein. For the purpose of the present invention, such conservative groups are set forth in Table 1 and are based on shared properties.

TABLE 1

Amino Acid Conservative Substitutions.

| Original Residue | Conservative Substitution |
| --- | --- |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

As used herein, an "antibody" means a monoclonal and polyclonal antibody and can belong to any antibody class (i.e., IgG, IgM, IgA, etc.). One of ordinary skill in the art is familiar with methods for making monoclonal antibodies (Mab). For example, one of ordinary skill in the art can make monoclonal antibodies by isolating lymphocytes and fusing them with myeloma cells, thereby producing hybridomas. See, e.g., Milstein C, "Handbook of experimental immunology," (Blackwell Scientific Pub., 1986); and Goding J, "Monoclonal antibodies: principles and practice," (Academic Press, 1983), each of which is incorporated herein by reference as if set forth in its entirety. The cloned hybridomas are then screened for production of, e.g., "anti-GPIbα" (i.e., antibodies that bind preferentially to GPIbα or fragments thereof)

or "anti-VWF" antibodies (i.e., antibodies that bind preferentially to VWF or fragments thereof). Monoclonal antibodies are thus not limited by the manner in which the antibodies are produced, whether such production is in situ or not. Alternatively, antibodies can be produced by recombinant DNA technology including, but not limited to, expression in bacteria, yeast, insect cell lines or mammalian cell lines.

Likewise, one of ordinary skill in the art is familiar with methods of making polyclonal antibodies. For example, one of ordinary skill in the art can make polyclonal antibodies by immunizing a suitable host animal, e.g., such as a rabbit, with an immunogen and using properly diluted serum or isolating immunoglobulins from the serum. The animal may therefore be inoculated with the immunogen, with blood subsequently being removed from the animal and an IgG fraction purified. Other suitable host animals include a chicken, goat, sheep, guinea pig, rat or mouse. If desired, the immunogen may be administered as a conjugate in which the immunogen is coupled, e.g., via a side chain of one of its amino acid residues, to a suitable carrier. The carrier molecule is typically a physiologically acceptable carrier. The antibody obtained may be purified to a purity of up to about 70%, up to about 80%, up to about 90%, up to about 95%, up to about 99% or up to about 100%.

Antibody also encompasses functional fragments, like Fab and F(ab')2, of anti-GPIbα or anti-VWF antibodies. Treatment of antibodies with proteolytic enzymes, such as papain and pepsin, generates these antibody fragments, especially anti-GPIbα fragments.

Antibodies are typically conjugated to a detectable label for easy visualization. Examples of suitable labels for the methods and kits described herein include, but are not limited to, radiolabels, biotin (which may be detected by avidin or streptavidin conjugated to peroxidase), lanthanides, alkaline phosphatase and fluorescent labels (e.g., fluorescein, rhodamine, especially the Alexa Fluor® family of fluorescent dyes available from Invitrogen/Molecular Probes). Labelling of the antibody can be carried out by, e.g. labeling free amine groups (covalently or non-covalently). Some labels can be detected by using a labeled counter suitable for the detection of the label in question.

Commercially available anti-GPIbα antibodies and anti-VWF antibodies are suitable for use with the methods and kits described herein, and can be obtained from Blood Research Institute (Milwaukee, Wis.) and Dako (Carpinteria, Calif.), respectively.

As shown in FIG. 1, the platelet adhesion receptor is comprised of a combination of four proteins, including GPIb, which is a heterodimer of an alpha chain (GPIbα; GenBank Accession No. NM_000173.4; SEQ ID NOS:1-2) and a beta chain (GPIbβ; GenBank Accession No. NM_000407.4; SEQ ID NOS:3-4) linked by disulfide bonds. Other components of the receptor include GP-V (GenBank Accession No. NM_004488.2; SEQ ID NOS:5-6) and GP-IX (GenBank Accession No. NM_000174.2; SEQ ID NOS:7-8). The platelet adhesion receptor binds to VWF (GenBank Accession No. NM_000552.3; SEQ ID NOS:9-10) to regulate hemostasis and thrombosis.

Of particular interest herein is human GPIbα modified so that a platelet aggregation agonist is not required in assays of VWF function. For example, GPIbα can be modified to include the gain-of-function mutations that cause platelet-type, pseudo VWD including, but not limited to, G233V (see, Miller J, et al., "Mutation in the gene encoding the alpha chain of platelet glycoprotein Ib in platelet-type von Willebrand disease," Proc. Natl. Acad. Sci. USA 88:4761-4765 (1991), incorporated herein by reference as if set forth in its entirety); D235V (see, Dong J, et al., "Novel gain-of-function mutations of platelet glycoprotein IBα by valine mutagenesis in the Cys209-Cys248 disulfide loop, which interacts with the A1 domain of VWF. Functional analysis under static and dynamic conditions," J. Biol. Chem. 275:27663-27670 (2000), incorporated herein by reference as if set forth in its entirety); M239V (see, Russell S & Roth G, "Pseudo-von Willebrand disease: a mutation in the platelet glycoprotein Ib alpha gene associated with a hyperactive surface receptor," Blood 81:1787-1791 (1993), incorporated herein by reference as if set forth in its entirety); G233S (Matsubara Y, et al., "Identification of a novel point mutation in platelet glycoprotein Ib, Gly to Ser at residue 233, in a Japanese family with platelet-type von Willebrand disease," J. Thromb. Haemost. 1:2198-2205 (2003)); and K237V (see, Dong et al., supra). Advantageously, the mutation(s) can be in the $Cys^{209}$-$Cys^{248}$ disulfide loop of GPIbα that compromise hemostasis by increasing the affinity of GPIb for VWF. For example, and as shown below, the inventor found that D235Y is another gain-of-function mutation suitable for use with the methods and kits described herein.

As used herein, a "functional fragment" means a fragment of a component of a platelet adhesion receptor, such as a fragment of GPIbα, having at least two of the previously mentioned mutation, yet retaining its ability to interact with VWF or other substrates. For example, the amino terminus of GPIbα retains its ability to interact with VWF. As shown below, fragments of GPIbα as small as 290 amino acids and having two mutations retained an ability to interact with VWF, although smaller fragments are contemplated. With respect to VWF, a functional fragment may comprise at least the A1 domain, which is the GPIb binding domain. With respect to antibodies, functional fragments are those portions of an antibody that bind to a particular epitope, such as the domains indicated above.

As used herein, a "sample" means a biological sample, such as amniotic fluid, aqueous humor, cerebrospinal fluid, interstitial fluid, lymph, plasma, pleural fluid, saliva, serum, sputum, synovial fluid, sweat, tears, urine, breast milk or tissue that has or is suspected of having VWF. With respect to measuring VWF, plasma is a suitable sample.

As used herein, a "surface" means, e.g., a cell surface or solid-phase surface, such as an unsoluble polymer material, which can be an organic polymer, such as polyamide or a vinyl polymer (e.g., poly(meth)acrylate, polystyrene and polyvinyl alcohol or derivates thereof), a natural polymer, such as cellulose, dextrane, agarose, chitin and polyamino acids, or an inorganic polymer, such as glass or plastic. The solid-phase surface can be in the form of a bead, microcarrier, particle, membrane, strip, paper, film, pearl or plate, particularly a microtiter plate.

One aspect of the present invention includes a diagnostic assay for measuring VWF. The underlying methodology of the assay can be FC, FACS or ELISA, each of which is well known to one of ordinary skill in the art. See, e.g., Alice Giva, "Flow cytometry: first principles," (2nd ed. Wiley-Liss, New York, 2001); Howard Shapiro, "Practical flow cytometry," (4th Ed. Wiley-Liss, New York, 2003); Larry Sklar, "Flow cytometry for biotechnology," (Oxford University Press, New York, 2005); J. Paul Robinson, et al., "Handbook of flow cytometry," (Wiley-Liss, New York, 1993); "Flow cytometry in clinical diagnosis," (3rd ed., Carey, McCoy and Keren, eds., ASCP Press 2001); Lequin R, "Enzyme immunoassay (EIA)/enzyme-linked immunosorbent assay (ELISA)," Clin. Chem. 51:2415-2418 (2005); Wide L & Porath J, "Radioimmunoassay of proteins with the use of Sephadex-coupled antibodies," Biochem. Biophys. Acta. 30:257-260 (1966);

Engvall E & Perlman P, "Enzyme-linked immunosorbent assay (ELISA). Quantitative assay of immunoglobulin G," Immunochemistry 8:871-874 (1971); and Van Weemen B & Schuurs A, "Immunoassay using antigen-enzyme conjugates," FEBS Letters 15:232-236 (1971), each of which is incorporated herein by reference as if set forth in its entirety.

As noted above, the surface for the methods and kits described herein can be a host cell surface expressing at least platelet GPIbα for use in FACS. For example, one can heterologously express (either transiently or stably) mutant GPIbα or other components of platelet adhesion receptor (i.e., GPIbβ and/or GP-IX) in host cells. Methods of expressing polynucleotides and their encoded platelet glycoprotein receptor polypeptides in heterologous host cells are known to one of ordinary skill in the art. See, e.g., Tait A, et al., "Phenotype changes resulting in high-affinity binding of von Willebrand factor to recombinant glycoprotein Ib-IX: analysis of the platelet-type von Willebrand disease mutations," Blood 98:1812-1818 (2001), incorporated herein by reference as if set forth in its entirety; and Dong et al., supra.

Cells suitable for use herein preferably do not natively display GPIbα or the other components of the platelet adhesion receptor complex. One such cell type is HEK-293T cells (American Type Culture Collection (ATCC); Manassas, Va.; Catalog No. CRL-11268). See also, Graham F, et al., "Characteristics of a human cell line transformed by DNA from human adenovirus type 5," J. Gen. Virol. 36:59-74 (1977), incorporated herein by reference as if set forth in its entirety. HEK-293 cells are easy to reproduce and to maintain, are amenable to transfection using a wide variety of methods, have a high efficiency of transfection and protein production, have faithful translation and processing of proteins and have a small cell size with minimal processes appropriate for electrophysiological experiments.

Another suitable cell type is COS-7 cells (ATCC; Catalog No. CRL-1651). See also, Gluzman Y, "SV40-transformed simian cells support the replication of early SV40 mutants," Cell 23:175-182 (1981), incorporated herein by reference as if set forth in its entirety. Like HEK-293 cells, COS-7 cells are easy to reproduce and maintain and are amenable to transfection using a wide variety of methods.

Yet another suitable cell type is Xenopus oocytes. Xenopus oocytes are commonly used for heterologous gene expression because of their large size (~1.0 mm), which makes their handling and manipulation easy. Xenopus oocytes are readily amenable to injection, and thus express functional proteins when injected with cRNA for an desired protein.

Yet another suitable cell type is S2 Drosophila melanogaster cells. S2 cells are ideal for difficult-to-express proteins, and a S2 expression system is commercially available from Invitrogen (Carlsbad, Calif.). The S2 expression system can be engineered to preferably lack the Bip secretion sequence so that the encoded proteins are expressed on the cell surface. Expression of platelet adhesion receptor components in S2 cells was previously shown by Celikel et al. See, Celikel R, et al., "Modulation of alpha-thrombin function by distinct interactions with platelet glycoprotein Ibα," Science 301:218-221 (2003), incorporated herein by reference as if set forth in its entirety.

Any of the contemplated polynucleotides for the platelet adhesion receptor can be cloned into an expression vector (or plurality of expression vectors) engineered to support expression from the polynucleotides. Suitable expression vectors comprise a transcriptional promoter active in a recipient host cell upstream of, e.g., a GPIbα polynucleotide engineered to have the previously mentioned mutations or additional polynucleotides and can optionally comprise a polyA-addition sequence downstream of the polynucleotide.

The vector(s) can be introduced (or co-introduced) by, for example, transfection or lipofection, into recipient host cells competent to receive and express mutant GPIbα and optionally other components of the platelet adhesion receptor. A commercially available lipofection kit, such as a kit available from Mirus Corporation (Madison, Wis.) can be employed. Preferably, the recipient host cells do not natively contain GPIbα, so that the presence of it is completely attributable to expression from the introduced expression vector. Suitable recipient host cells are described above and can express the polypeptides on their surface or secrete them.

Alternatively, the surface for the methods and kits described herein can be a solid-phase surface having platelet GPIbα immobilized thereupon by, e.g., covalent attachment or antibodies. Suitable solid-phase surfaces include the solid-phase surfaces described above. One of ordinary skill in the art is familiar with methods for attaching anti-GPIbα antibodies or functional fragments thereof to solid-phase surfaces. For example, the antibody or functional fragment thereof can be immobilized on the surface directly by covalent coupling or via a carrier such as a linker molecule or an antibody immobilized on the solid-phase surface. The antibody can be a polyclonal or monoclonal antibody, such as anti-GPIbα or a functional fragment thereof. Alternatively, the antibody can be an anti-epitope antibody that recognizes an epitope-tag (e.g., biotin, digoxigenin, GST, hexahistidine, hemagglutinin, FLAG™, c-Myc, VSV-G, V5 and HSV) complexed with GPIbα. Commercially available epitope tags and their respective antibodies are suitable for use with the methods and kits described herein, and can be obtained from Sigma Aldrich (St. Louis, Mo.) and Abcam, Inc. (Cambridge, Mass.).

The methods and kits described herein are thus sensitive to the measurement of the more functional, large VWF multimers, correlates with VWF:Ag in individuals with reduced VWF function, and remains unaffected by mutations that affect VWF binding of ristocetin but do not have a bleeding phenotype.

The invention will be more fully understood upon consideration of the following non-limiting Examples.

EXAMPLES

Example 1

Cells Heterologously Expressing Mutant GPIbα Spontaneous Binding in the Absence Ristocetin Methods: A heterologous platelet adhesion receptor expression system was constructed by transiently transfecting HEK-293T cells (ATCC) with a full-length GPIbα construct encoding a single mutation (i.e., G233V, D235Y or M239V), a double mutation (i.e., G233V/M239V, G233V/D235Y or D235Y/M239V) a triple mutation (i.e., G233V/D235Y/M239V) relative to SEQ ID NO:2 or wild-type GPIbα (SEQ ID NO:2). Some HEK-293T cells also were transiently transfected with GPIbβ and GP-IX constructs encoding SEQ ID NOS:4 and 8, respectively. A mock group of HEK-293T cells were treated similarly, but were transfected with an expression vector lacking the above constructs, thereby serving as controls.

The constructs were cloned in to a pCI-neo vector (Promega; Madison, Wis.) and expressed in HEK-293T cells as described below. In some instances, separate constructs were made for each GPIbα mutation; however, in other instances, a single construct was made having multiple GPIbα mutations.

Briefly, HEK-293T cells were first seeded until they were 50-80% confluent (i.e., $3.5$-$4 \times 10^6/100$ mm dish). Typically, the cells were seeded the day before transfection.

For transfection, Hanks Balanced Salt Solution (HBSS) and OptiMEM (Invitrogen) were warmed to 37° C. 800 µl of OptiMEM was added to 17×100 polystyrene tubes (2 tubes/plate to be transfected). The following was added to one set of tubes: 4.5 µg of DNA (1.5 µg of each construct) and 20 µl PLUS Reagent (Invitrogen). The following was added to another set of tubes: 30 µl Lipofectamine (Invitrogen). Each set was allowed to incubate at room temperature for 15 minutes. The DNA mixture was then added to the Lipofectamine mixture and incubated at room temperature for 15 minutes. During incubation, the cells were washed twice with 5 ml HBSS. 3.4 ml of OptiMEM was added to the DNA/Lipofectamine mixture, and then added to the HEK-293T cells (total volume=5 ml). The cells were then incubated at 37° C. with 5% $CO_2$ for 3-3.5 hours.

Following transfection, the transfection medium was removed and 8 ml of fresh complete medium was added to the cells. The cells were then incubated at 37° C. with 5% $CO_2$ for about 60 hours. Cells were then harvested for use in a standard FACS assay using ristocetin.

For FACS, about 50 µl of a 1:10 dilution of platelet poor plasma (PPP; source of VWF) in assay buffer was added to the plate and serially diluted 1:2 to final dilution of 1:80. ISTH Lot #3 (GTI; Milwaukee, Wis.) was used as a standard and diluted 1:10 in assay buffer and serially diluted 1:2 to a final dilution of 1:320. The plate was then incubated for one hour at room temperature. After the one-hour incubation, the plate was centrifuged again at 1200 rpm for 5 minutes and the supernatant was discarded.

In some experiments, the PPP was diluted in PBS containing 1% BSA and either 1 mg/ml Ristocetin A (American Biochemical & Pharmaceuticals, Ltd.; Marlton, N.J.) or 1 mg/ml Botrocetin (Sigma Aldrich).

Fluorescently labeled antibodies (anti-GPIbα; Blood Research Institute) were diluted to a final concentration of 5 µg/ml in assay buffer. Fluorescently labeled anti-VWF polyclonal was also was diluted to a final concentration of 5 µg/ml in assay buffer and added to transfected cells incubated in PPP. Normal rabbit IgG (NRIgG; Pierce) and AP-1 were added at a concentration of 5 µg/ml to transfected cells as negative and positive controls, respectively. The plate was then incubated in the dark for one hour at room temperature. Assay buffer was added to each well to bring the final volume to 150 µl, and FACS was performed using a BD LSRII System (Becton Dickinson). Results are shown in VWF:IbCo units.

Figure 2:
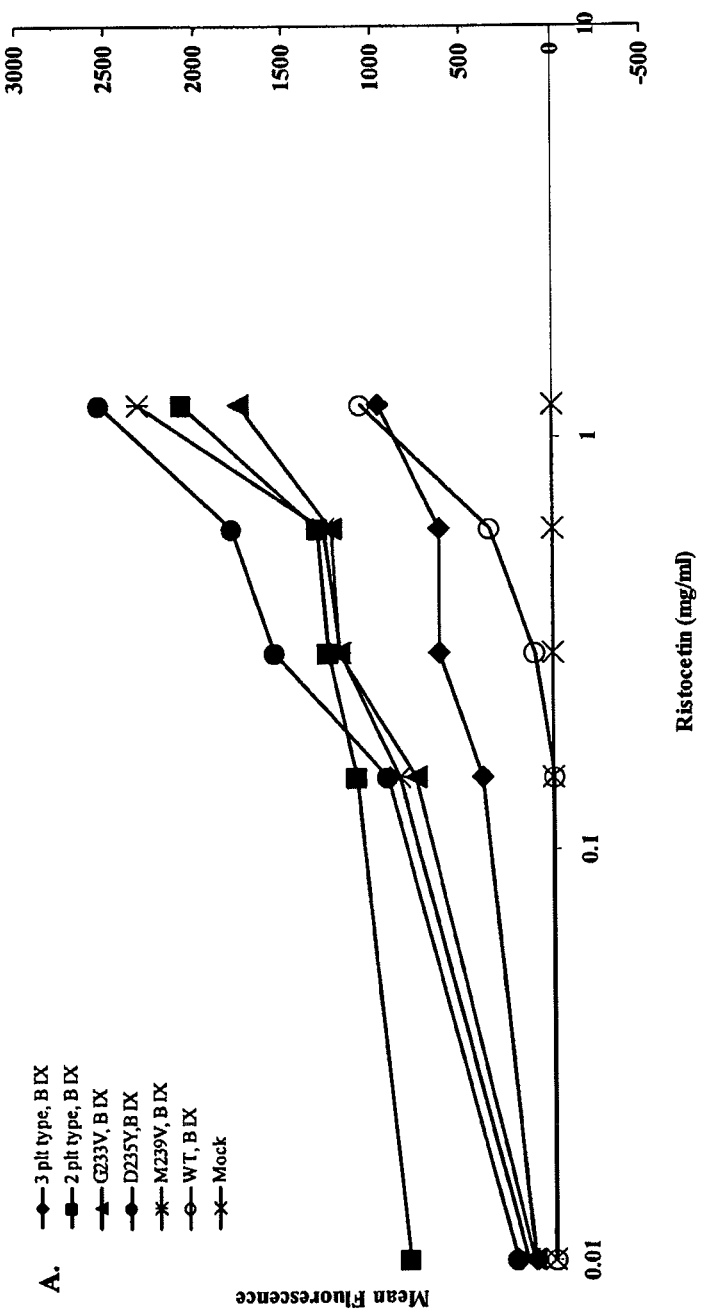
FIGS. 2A-C show the effect GPIbα mutations (single, double or triple.
Figure 2:
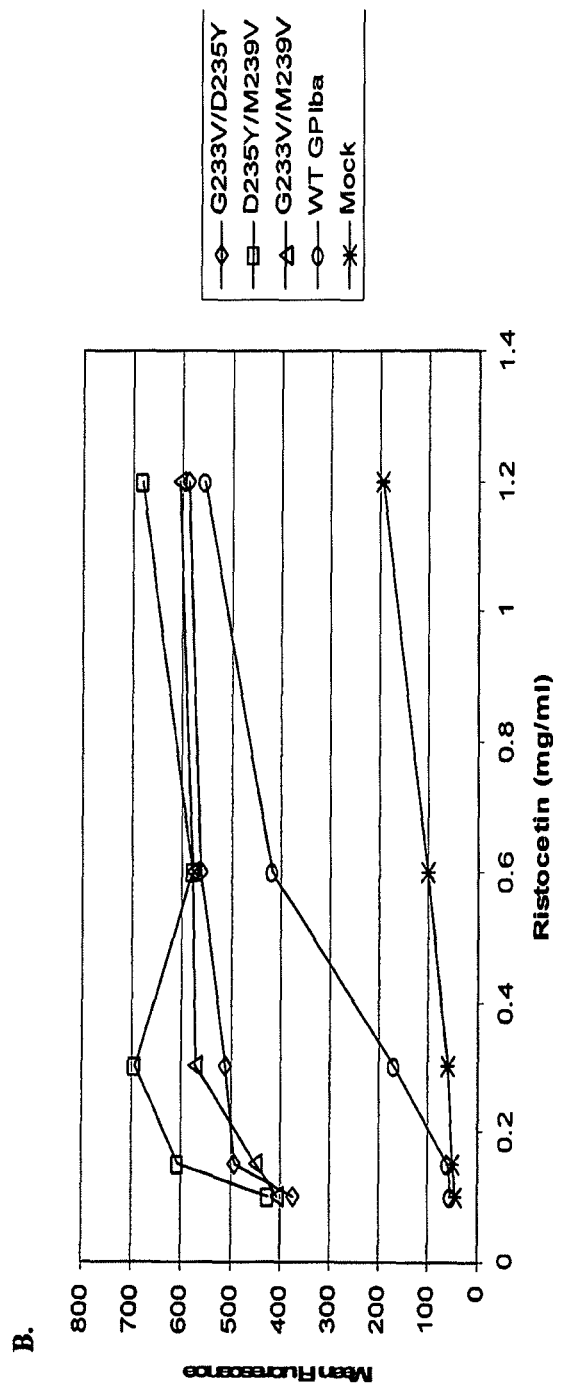
Figure 2:
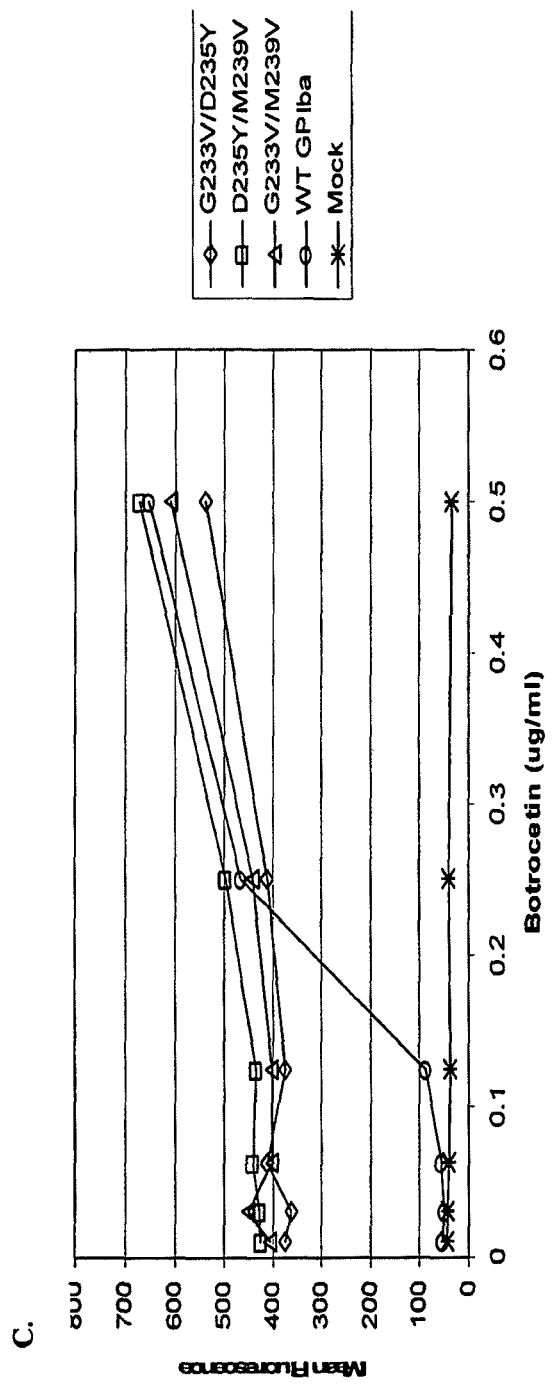

Results: As shown in FIG. 2A, mock transfected HEK-293T cells did not show any binding in the presence of ristocetin, while cells expressing wild-type GPIbα showed a concentration-dependent decrease in ristocetin binding after 1.2 mg/ml. HEK-293T cells expressing only one of the GPIbα mutations showed increased sensitivity even at low concentrations of ristocetin, which suggests that the binding is independent of ristocetin. Cells expressing two GPIbα mutations showed an extreme sensitivity to ristocetin or alternatively, an increased spontaneous binding that was independent of ristocetin. HEK-293T cells expressing the triple GPIbα mutation (i.e., G233V/D235Y/M239V), however, did not show increased sensitivity/spontaneous binding relative to the double mutants. As shown in FIG. 2B, each of the double mutants (i.e., G233V/M239V, G233V/D235Y or D235Y/M239V) showed comparable spontaneous binding relative to one another that was not significantly affected by ristocetin (i.e., ristocetinless). As expected the, wild-type control showed concentration-dependent increases in VWF:IbCo to ristocetin. As shown in FIG. 2C, VWF:IbCo is not affected by the type of platelet aggregation agonist, as none of the double mutants was significantly affected by botrocetin (i.e., botrocetinless). As expected, wild-type control showed concentration-dependent increases in VWF:IbCo to botrocetin.

Example 2

VWF Function in Patient Samples Using Mutant GPIbα in FACS

Methods: HEK293T cells were transiently transfected with a wild-type GPIbα construct or GPIbα encoding one of the double mutants, as described above. The cells were additionally transfected with the GPIbβ and GP-IX constructs. A group of HEK-293T cells were mock transfected, as describe above.

After forty-eight hours, the transfected cells were lifted from the plate with 3 mM EDTA, resuspended in assay buffer (i.e., 1×PBS containing 2% BSA) and counted. Trypsin was not used, as it potentially can cleave GPIbα from the cell surface. After counting, $1.75 \times 10^5$ cells were plated 96-well plate (Becton Dickinson; Franklin Lakes, N.J.) as a way of standardizing GPIbα on the plate surface, and the plate was then centrifuged at 2000 rpm for 5 minutes to pellet the cells. The supernatant was discarded.

HEK-293T cells expressing the GPIbα mutations were used in flow cytometry assays to test VWF binding, which was measured with a fluorescently labeled anti-VWF polyclonal antibody from Dako. A normal curve was developed using serial dilutions of reference plasma previously standardized against both the ISTH and WHO VWF standards based on the VWF:Ag international standard that is also standardized for VWF:RCo.

In one set of experiments, normal patient samples were used to determine whether the HEK-293T cells required all components of the platelet adhesion receptor or simply GPIbα. Normal patient samples were used. In another set of experiments, patient samples from normal individuals and individuals having VWD were used in the FACS assay as described above in Example 2.

Samples included 41 normals, 16 type-2M VWD, 5 type-2B VWD and 5 type-2A VWD plasma, Included therein were individuals with apparent type-2M VWD, but without clinical symptoms, and African Americans with a reduced VWF:RCo/VWF:Ag (RCo/Ag) ratio. Of the 16 type-2M VWD samples, 7 had markedly reduced VWF:IbCo (consistent with the VWF:RCo assay), and 9 had normal VWF:IbCo. African Americans with SNPs associated with reduced RCo/Ag ratios had VWF:IbCo assays that correlated with their VWF:Ag in contrast to the abnormal RCo/Ag ratios identified by standard assays. Type-2A individuals exhibited reduced VWF:IbCo assays and multimer size seemed to correlate with VWF:IbCo activity. Thus, measurement of VWF function using the VWF:IbCo assay more directly correlates with VWF function and avoids some of the pitfalls and functional variability of VWF:RCo assays.

Results: As shown in Table 2, GPIbβ and GP-IX are not required for surface expression of the mutant GPIbα, as FACS results from HEK-293T cells expressing multiple components of the plate adhesion receptor were not significantly different from cells expressing only GPIbα.

TABLE 2

Effect of GPIbα Having a Double Mutation With or Without the Other Platelet Adhesion Receptor Components in a FACS.

| Sample | Known VWF:RCo (IU/dL) | GPIbα (G233V/M239V), GPIbβ and IX | GPIbα | % Diff btw Transfections | % Diff. btw GPIbα, GPIbβ and IX & Known | % Diff. btw GPIbα & Known |
|---|---|---|---|---|---|---|
| ISTH 2 | 71 | 70.4 | 70.3 | 0.1 | 0.4 | 0.5 |
| ISTH 3 | 86 | 86.9 | 91.4 | 2.5 | 0.5 | 3.0 |
| CCNRP | 82 to 103 | 89.0 | 74.6 | 8.8 | 4.1 | 4.7 |
| Cntrl 3 | 65 | 64.4 | 52.1 | 10.5 | 0.5 | 11.0 |
| Cntrl 4 | 24.6 | 26.7 | 22.7 | 8.0 | 4.0 | 4.1 |
| JS | 0 | 0 | 0 | 0 | 0 | 0 |
| XX-01 | 200 | 136.4 | 119.5 | 6.6 | 18.9 | 25.2 |

ISTH = reference sample

As shown below in Table 3, the FACS assay resulted in VWF measurements comparable to a method used in clinical laboratories. Samples were normal individuals and individuals having VWD. Table 4 is similar to Table 3, except that the samples were from normal individuals and individuals having Type 2 VWD. Table 5 is also similar to Table 3, except that the samples were from individuals having Type 2M VWD.

TABLE 3

Summary of VWF:IbCo by FACS in Plasma Samples from African Americans and Caucasians with and without VWF Single Nucleotide Polymorphisms (SNPs).

| Sample | VWF:Ag 1 | VWF:RCo | Ratio 1 | VWF:Ag 2 | VWF:IbCo | Ratio 2 | Ratio 2/Ratio 1 |
|---|---|---|---|---|---|---|---|
| IN-09 | 215 | 104 | 0.484 | 167 | 131 | 0.784 | 0.608 |
| XX-22 | 193 | 140 | 0.725 | 152 | 240 | 1.579 | 1.244 |
| XX-24 | 278 | 225 | 0.809 | 233 | 240 | 1.029 | 0.863 |
| XX-27 | 195 | 130 | 0.667 | 186 | 147 | 0.788 | 0.753 |
| XX-29 | 85 | 74 | 0.871 | 79 | 104 | 1.313 | 1.222 |
| AT-09 | 103 | 69 | 0.670 | 88 | 78 | 0.886 | 0.756 |
| AT-13 | 71 | 72 | 1.014 | 72 | 89 | 1.226 | 1.251 |
| AT-14 | 257 | 248 | 0.965 | 231 | 233 | 1.009 | 0.906 |
| AT-17 | 225 | 95 | 0.422 | 188 | 144 | 0.766 | 0.641 |
| AT-18 | 225 | 195 | 0.867 | 186 | 155 | 0.834 | 0.689 |
| XX-21 | 85 | 92 | 1.082 | 90 | 72 | 0.801 | 0.844 |
| AT-06 | 154 | 176 | 1.143 | 150 | — | — | — |
| IN-15 | 122 | 85 | 0.697 | 83 | 140 | 1.685 | 1.146 |
| PB-06 | 86 | 88 | 1.023 | 78 | 137 | 1.755 | 1.594 |
| PB-14 | 234 | 211 | 0.902 | 238 | 197 | 0.831 | 0.843 |
| PB-17 | 109 | 93 | 0.853 | 104 | 68 | 0.649 | 0.620 |
| AT-16 | 82 | 94 | 1.146 | 73 | 94 | 1.284 | 1.143 |
| AT-19 | 164 | 151 | 0.921 | 147 | 126 | 0.859 | 0.771 |
| AT-42 | 86 | 69 | 0.802 | 70 | 64 | 0.902 | 0.710 |
| NO-53 | 243 | 252 | 1.037 | 239 | 159 | 0.666 | 0.655 |
| DT-08 | 68 | 71 | 1.044 | 58 | 62 | 1.064 | 0.910 |
| DT-01 | 88 | 107 | 1.216 | 91 | 82 | 0.906 | 0.937 |
| DT-06 | 82 | 79 | 0.963 | 83 | 82 | 0.981 | 0.995 |
| XX-04 | 96 | 109 | 1.135 | 86 | 128 | 1.481 | 1.334 |
| XX-06 | 129 | 149 | 1.155 | 111 | 128 | 1.148 | 0.993 |
| XX-13 | 124 | 169 | 1.363 | 114 | 186 | 1.638 | 1.503 |

TABLE 3-continued

Summary of VWF:IbCo by FACS in Plasma Samples from African
Americans and Caucasians with and without VWF Single Nucleotide Polymorphisms (SNPs).

| | | | | | | | |
|---|---|---|---|---|---|---|---|
| IN-13 | 103 | 92 | 0.893 | 100 | 88 | 0.887 | 0.859 |
| IN-22 | 96 | 110 | 1.146 | 104 | 65 | 0.627 | 0.678 |
| PB-09 | 88 | 78 | 0.886 | 100 | 77 | 0.767 | 0.870 |
| XX-03 | 106 | 136 | 1.283 | 103 | 160 | 1.551 | 1.511 |
| XX-12 | 137 | 183 | 1.336 | 128 | 189 | 1.437 | 1.380 |
| XX-14 | 115 | 163 | 1.417 | 109 | — | — | — |
| XX-15 | 123 | 137 | 1.114 | 159 | 122 | 0.768 | 0.992 |
| IN-01 | 209 | 220 | 1.053 | 149 | — | — | — |
| IN-03 | 71 | 68 | 0.958 | 68 | 54 | 0.801 | 0.762 |
| IN-07 | 95 | 85 | 0.895 | 77 | 76 | 0.995 | 0.802 |
| PB-01 | 84 | 77 | 0.917 | 82 | 71 | 0.862 | 0.805 |
| PB-04 | 155 | 162 | 1.045 | 146 | 105 | 0.722 | 0.678 |
| PB-20 | 107 | 114 | 1.065 | 91 | 95 | 1.046 | 0.855 |
| NO-23 | — | — | — | 143 | <1.1 | — | — |

1 = DT method (a clinical laboratory method)
2 = BRI method (Blood Research Institute method)
Shaded area = <0.81

TABLE 4

VWF:IbCo by FACS in Plasma from African Americans and Caucasians With/Without Type 2 VWD and Repeats.

| Sample | Race | VWD Phenotype | VWF Mutation | VWF:Ag | VWF:RC0 | RC0/Ag | FACS1 | FACS1/Ag | FACS2 | FACS2/Ag |
|---|---|---|---|---|---|---|---|---|---|---|
| DB | AA | "2M" | 3 AA snps | 86 | 47 | 0.547 | 78 | 0.910 | 78 | 0.905 |
| MK0055 | AA | "2M" | P1467S | 257 | 36 | 0.140 | 214 | 0.833 | 184 | 0.718 |
| LJ | C | "2M" | 3 AA snps | 66 | 40 | 0.606 | 180 | 2.734 | 48 | 0.735 |
| IN0061 | | 2M | R1374C | 22 | 11 | 0.500 | 4 | 0.204 | 10 | 0.432 |
| RH | | 2B | R1308S | 43 | 37 | 0.860 | 67 | 1.558 | 67 | 1.557 |
| LB | | 2B | V1316M | 91 | 62 | 0.681 | 159 | 1.751 | 106 | 1.162 |
| SB | | 2B | V1316M | 27 | 12 | 0.444 | 36 | 1.347 | 25 | 0.914 |
| AJ | | 2B | H1268D | 21 | 17 | 0.810 | 31 | 1.484 | 41 | 1.959 |
| PB0068 | | 2B | R1306W | 23 | 13 | 0.565 | — | — | 25 | 1.065 |
| YG | | 2A | L1503P | 26 | 13 | 0.500 | — | — | 19 | 0.714 |
| AV | | 2A | G1579R | 46 | 16 | 0.348 | — | — | 1 | 0.028 |
| AT0021 | | 2A | M7401? | 31 | 12 | 0.387 | — | — | 18 | 0.574 |
| AT0032 | | 2A | I1628T | 120 | 32 | 0.267 | — | — | 103 | 0.586 |
| IA0001 | | 2A | R1597W | 33 | <10 | — | — | — | 8 | 0.247 |
| AT0017 | AA | NL | 3 AA snps | 225 | 95 | 0.422 | 144 | 0.641 | 156 | 0.695 |
| XX0027 | AA | NL | 3 AA snps | 195 | 130 | 0.677 | 147 | 0.753 | 116 | 0.595 |
| XX0004 | C | NL | — | 96 | 109 | 1.135 | 128 | 1.334 | 114 | 1.183 |
| XX0013 | C | NL | — | 124 | 169 | 1.363 | 186 | 1.503 | 105 | 0.843 |
| PB0014 | AA | NL | — | 234 | 211 | 0.902 | 197 | 0.843 | 213 | 0.909 |
| AT0042 | AA | NL | — | 86 | 69 | 0.802 | 64 | 0.739 | 91 | 1.056 |

AA = African American
C = Caucasian
NL = normal
"2M" = apparent type 2M

TABLE 5

VWF Function in Plasma from African Americans and Caucasians With/Without Type 2 M VWD.

| Sample | Race | VWD Phenotype | VWF Mutation | VWF:Ag 1 | VWF:RC0 1 | RC0/Ag 1 | FACS2 | FACS2/Ag |
|---|---|---|---|---|---|---|---|---|
| TB | C | "2M" | — | 127 | 87 | 0.69 | 87 | 0.69 |
| DB | AA | "2M" | 3 AA snps | 86 | 47 | 0.55 | 78 | 0.91 |
| AC | C | 2M | G13242S | 95 | 13 | 0.14 | <1.1 | — |
| BF | — | 2M | I1416T (new) | 89 | 31 | 0.35 | 36 | 0.41 |

TABLE 5-continued

VWF Function in Plasma from African Americans and Caucasians With/Without Type 2 M VWD.

| Sample | Race | VWD Phenotype | VWF Mutation | VWF:Ag 1 | VWF:RCO 1 | RCO/Ag 1 | FACS2 | FACS2/Ag |
|---|---|---|---|---|---|---|---|---|
| MG | H | 2M | I1425F | 45 | 16 | 0.36 | >1.1 | — |
| LG | C | 2M | E1359K | 67 | 37 | 0.55 | 27 | 0.41 |
| GI | — | 2M | D1283H (new) | 16 | 4 | 0.25 | <1.1 | — |
| KJ | C | 2M | — | 12 | 3 | 0.25 | <1.1 | — |
| LJ | AA | "2M" | 3 AA snps | 66 | 40 | 0.61 | 180 | 2.73 |
| BM | C | 2M | I1426T | 156 | 43 | 0.28 | 93 | 0.60 |
| AR | — | 2M | R1374L | 48 | 10 | 0.21 | <1.1 | — |
| DR | AA | "2M" | R1342C; I1343V; 1301-3103 del; and R2185Q | 38 | 12 | 0.32 | 37 | 0.97 |
| MK0038 | C | 2M | R1392-Q1402 del | 47 | 11 | 0.23 | <1.1 | — |
| IN0061 | C | 2M | R1374C | 22 | 11 | 0.50 | 4 | 0.20 |
| MK0055 | AA | "2M" | P1467S | 257 | 36 | 0.14 | 214 | 0.83 |
| MK0058 | AA | "2M" | P1467S | 265 | 68 | 0.14 | 194 | 0.73 |

AA = African American
C = Caucasian
H = Hispanic

Figure 4:
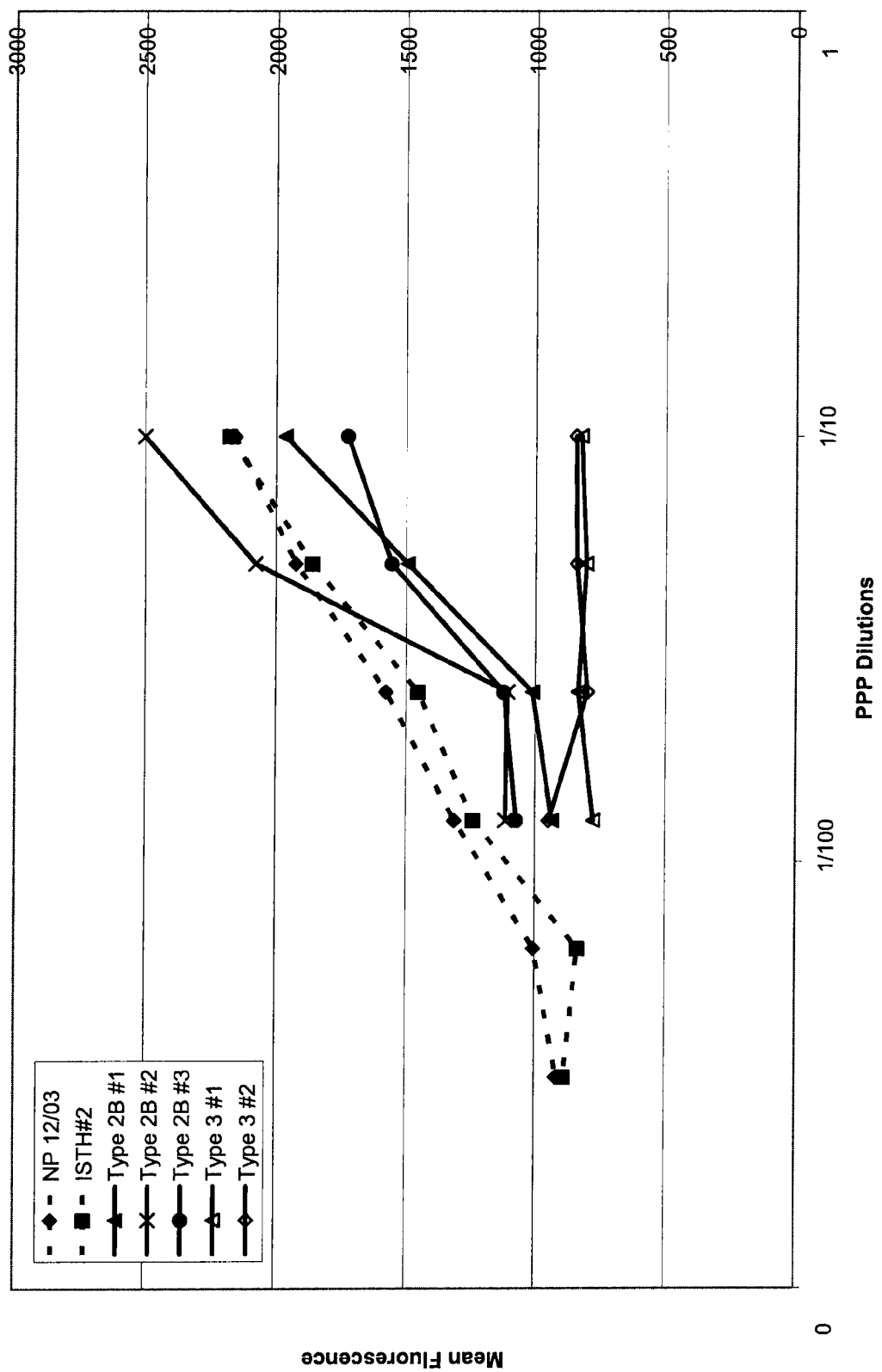
FIG. 4 shows an FACS assay with additional samples from individuals having type 2B VWD, which has gain-of-function VWF mutations (y-axis is mean fluorescence and x-axis is platelet poor plasma (PPP) dilutions).

Results: As shown in FIG. 4, individuals with normal VWF showed a typical increase in mean fluorescence with lower dilutions of their plasma. As expected, individuals with Type 3 VWD showed change in mean fluorescence because their plasma has low or no VWF.

Figure 5:
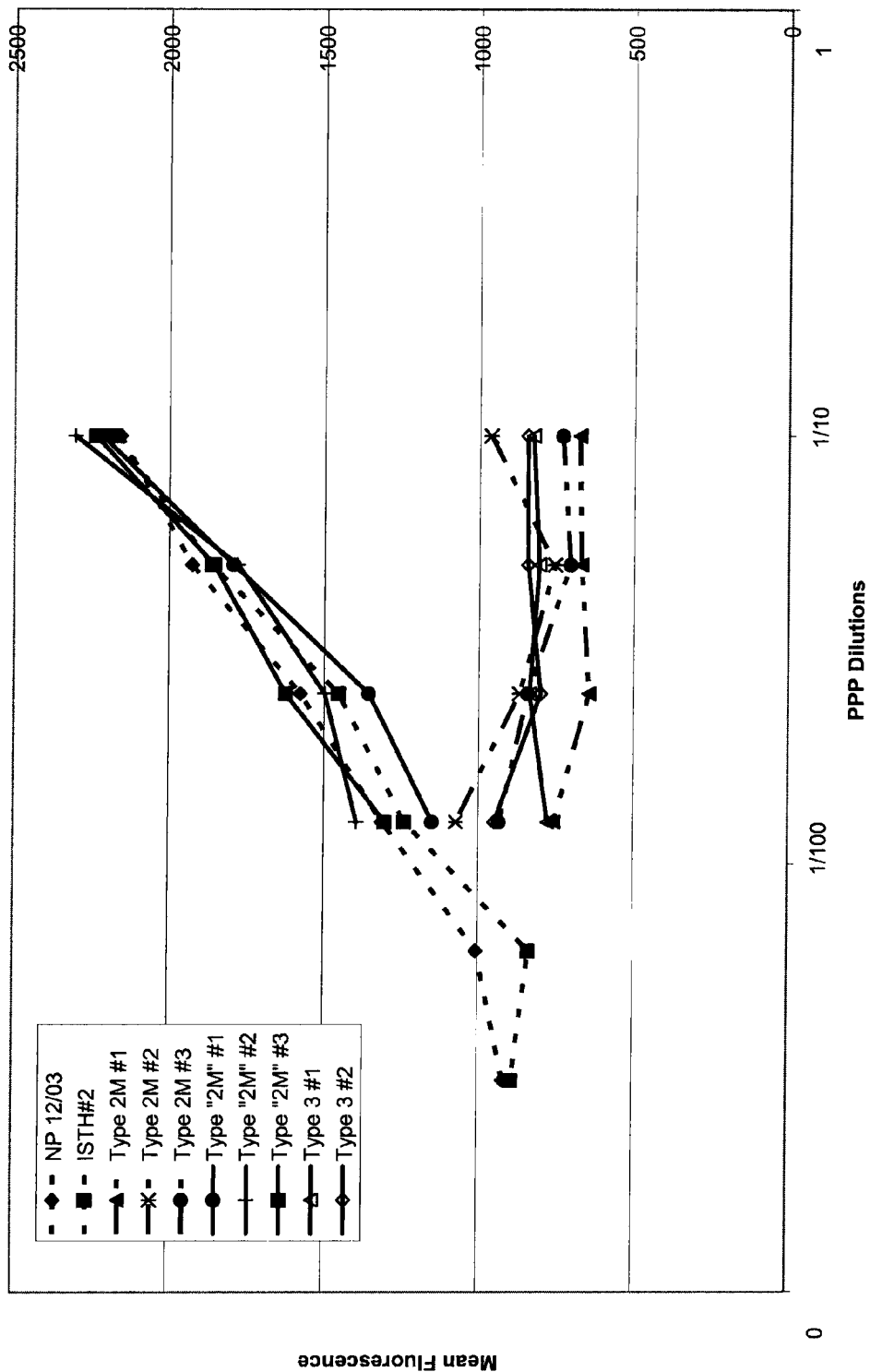
FIG. 5 shows a FACS assay with additional samples from individuals having type 2M VWD, which has low GPIb binding, and apparent type 2M VWD, which has low VWF:RCo/VWF:Ag, yet normal levels of VWF (y-axis is mean fluorescence and x-axis is platelet poor plasma (PPP) dilutions).

As shown in FIG. 5, individuals with Type 2B VWD showed a much earlier increase in mean fluorescence when compared to normals, starting at very high dilutions of their plasma (i.e., >1/100). Type 2B VWD is characterized as having gain-of-function mutations. Again, individuals with Type 3 VWD showed no reaction in the assay.

Figure 6:
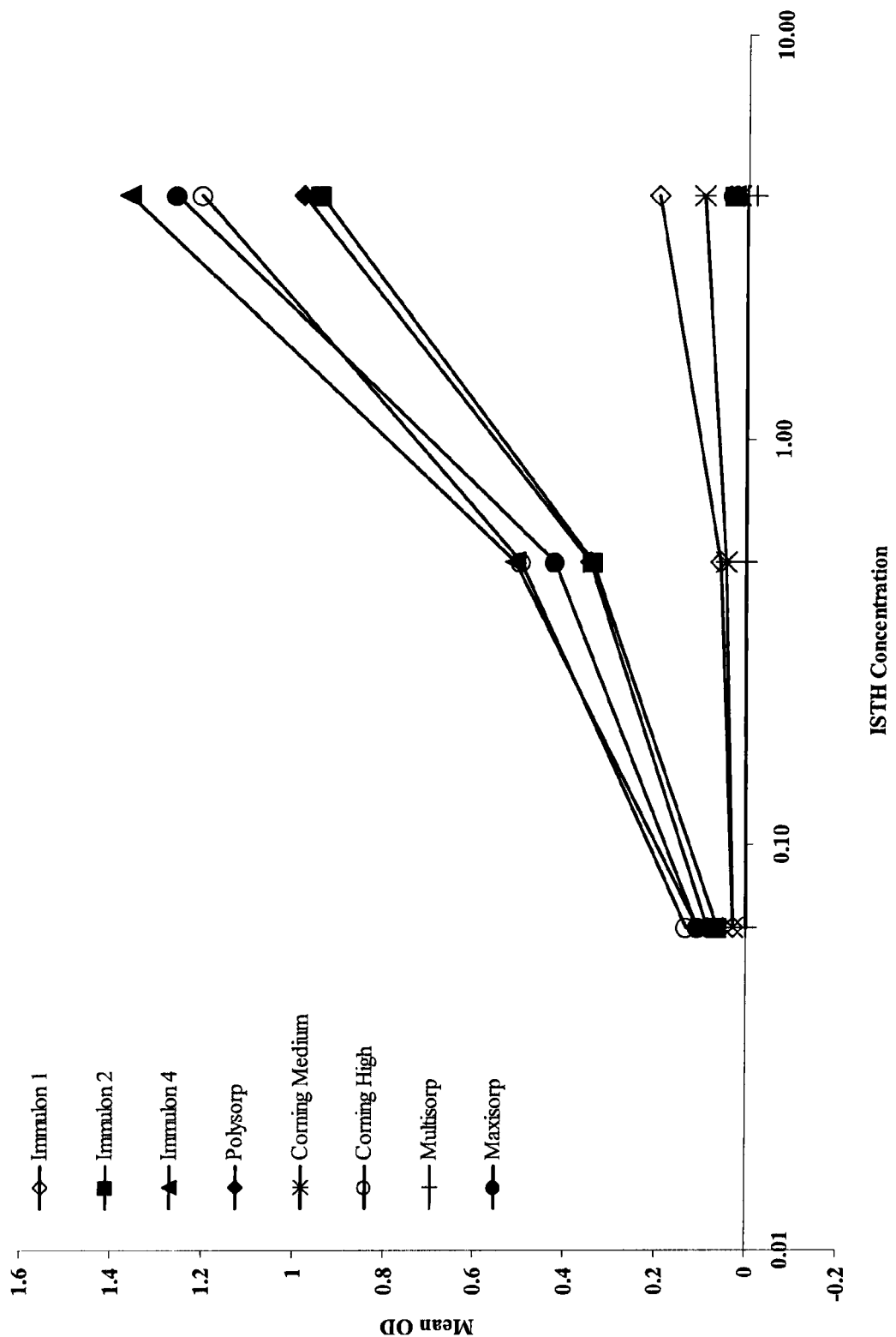
FIG. 6 shows the effect of charge on the solid-phase surface during an ELISA with immobilized GPIbα having two platelet-type, pseudo VWD mutations (y-axis is mean fluorescence and x-axis is ISTH (a standard) concentration in U/dL).

As shown in FIG. 6, individuals with Type 2M VWD showed no increase in mean fluorescence when compared to normals. Type 2M VWD is characterized by defective VWF that does not interact with GPIbα. Individuals with apparent Type 2M ("2M") showed a much earlier increase in mean fluorescence when compared to normals, starting at very high dilutions of their plasma (i.e., >1/100). Apparent Type 2M is characterized by low VWF:RCo/VWF:Ag, yet normal levels of VWF. Again, individuals with Type 3 VWD showed no reaction in the assay.

Example 3

Mutant GPIbα Function in ELISA

S2 cells (Invitrogen) were stably transfected with a mutant GPIbα construct, a wild-type GPIbα construct and a GP-IX construct. In some experiments, S2 cells were transfected with GPIbα constructs having a C65A mutation and ΔTM290 mutation. The C65A mutation removed a cysteine that could potential allow dimerization of GPIbα; and the ΔTM290 mutation removed the transmembrane region so that the expressed protein was excreted.

Briefly, the constructs were cloned into a pMT/Bip/V5-His:GPIbα C65A, D235Y, M239V ΔTM290 or pMT/Bip/V5-His:GPIbα C65A ΔTM290 secretion vector (Invitrogen). On day 1, S2 cells were counted and seeded into a 35 mm dish or a well of a 6 well plate at $3\times10^6$ cells in 3 ml of complete medium (Ex-Cell 420+10% FBS+7 mM L-Glutamine). The cells were allowed to grow 6-8 hours at 28° C. The following was added to one set of tubes: Solution A, which contained 36 μl of 2M $CaCl_2$, 19 μg of plasmid DNA (purified with Qiagen Maxi Kit; Qiagen; Valencia, Calif.), 1 μg pCoBlast (selection vector) and $ddH_2O$ up to 300 μl. The following was added to another set of tubes: Solution B, which contained 300 μl of 2×HEPES buffered saline. Solution A was slowly added dropwise to solution B while gently vortexing. The combined solutions then were incubated at room temperature for 30-40 minutes until a fine precipitate formed.

The mixed solution was added dropwise to the plated cells while gently swirling the plate. The cells were then incubated overnight at 28° C. (about 16-24 hours).

The next day, the transfection solution was removed and replaced with 3 ml of fresh complete medium and incubated at 28° C. without $CO_2$. On day 5, the cells were resuspended cells and transferred to a 15 cc conical tube, centrifuged at 2400 rpm for 2 minutes. The medium was decanted, and the cells were resuspended in 3 ml of stable medium (complete medium+25 μg/ml Blastidin-S) and plated in a new dish or well.

Selection began on week 2. As done on Day 5, the selection medium was replaced every 3-4 days with 3 ml fresh selection medium. Selection and expansion continued through week 3. During this time, the cells were resuspended, transferred to 15 cc conical tubes, and centrifuged at 2400 rpm for 2 minutes. The media as decanted, and the cells were resuspended in 5 ml of selector media and plated in new T25 flask. After 4 days, the cells were expanded from 1 T25 to 2 T25 flasks.

Expansion and freezing stocks began on week 4. Cells were expanded from the T25 flasks to T75 flasks ($3\times10^6$ cells/ml medium). T75 flasks received 15 ml medium, which was about $45\times10^6$ cells. The remaining cells (about $2\times10^7$ cells/vial) were frozen and stored in liquid nitrogen.

Induction of the cells in the T75 flasks began on week 5. Cells were resuspended, transferred to a 15 cc conical tube for counting and centrifuged. $45\times10^6$ cells were resuspended 15 ml induction medium (stable medium+500 μM $CuSO_4$) and transferred to T75 flasks. The cells were then incubated 4 days at 28° C., the supernatant having secreted GPIbα was harvested.

Figure 3:
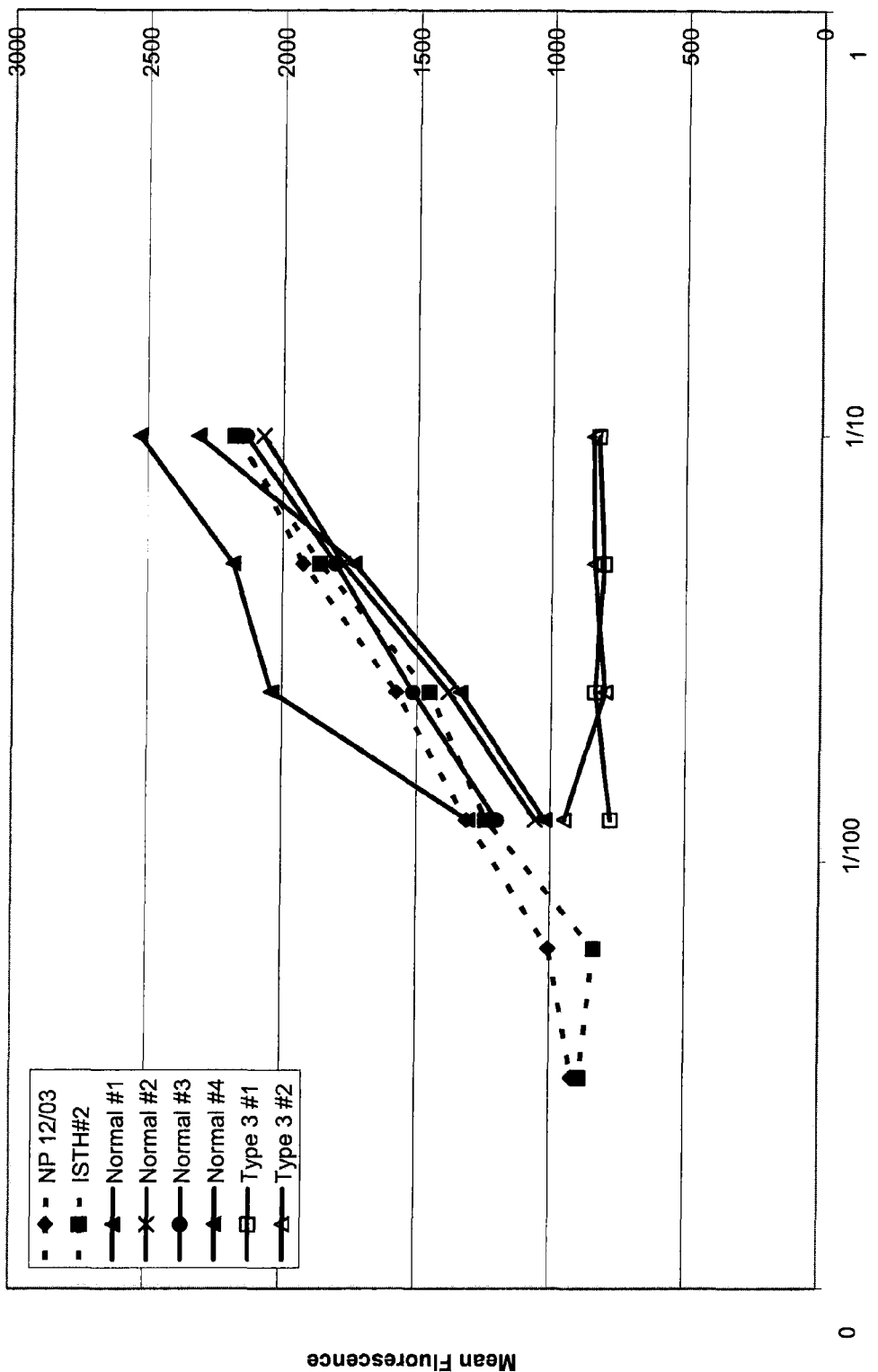
FIG. 3 shows an FACS assay with GPIbα having two platelet-type, pseudo VWD mutations using samples from control individuals and with type 3 VWD, which has low to undetectable VWF (y-axis is mean fluorescence and x-axis is platelet poor plasma (PPP) dilutions).

As shown Table 6 and FIG. 3, various solid-phase surfaces were first tested for the ELISA assays. Table 6 shows that the surface density of GPIbα was affected by the surface charge of the solid-phase surface; whereas FIG. 3 shows that different solid-phase surfaces coated with GPIbα having a double mutation affected VWF binding. Solid-phase surface charge appeared to affect GPIbα/VWF binding, suggesting that any solid-phase surface should first be tested for it ability (1) to provide a uniform density of GPIbα and (2) to permit VWF to bind to the GPIbα. After considering both Table 6, and FIG. 3, Immulon® 4 HBX Plates worked best and were used thereafter.

TABLE 6

Effect of Various Solid-Phase Surfaces on Concentration of GPIbα Double Mutation (G233V/M239V) (same samples on different plates).

| Solid-Phase Surface | Characteristic of the Surface | Calculated GPIbα concentration |
|---|---|---|
| Immulon 1 | Hydrophobic | 635.1 |
| Immulon 2 | Hydrophobic | 370.8 |
| Immulon 4 | Maximum | 383.7 |
| Polysorp | Hydrophobic | 321.7 |
| Corning Medium | Hydrophobic | 576.8 |
| Corning High | Ionic and/or Hydrophobic | 414.7 |
| Multisorb | Polar Molecules | No binding |
| Maxisorb | Hydrophobic/Hydrophilic | 408.5 |

An Immulon® 4 HBX Plate (Thermo Scientific; Waltham, Mass.) was coated with anti-GPIbα monoclonal antibody 142.16 (Blood Research Institute) at a concentration of 5 μg/ml, which was then incubated overnight at 4° C. The plate was blocked with PBS containing 1% BSA for 1 hour at room temperature. Nickel-purified S2-expressed proteins—GPIbα C65A, D235Y, M239V and ΔTM290-were diluted in PBS containing 1% BSA and incubated on the anti-GPIbα antibody-coated plate for 1 hour at 37° C. See, Celikel et al., supra.

PPP from controls or individuals having VWD was diluted 1:50 in PBS containing 1% BSA and serially diluted 1:2 to a final dilution of 1:100. Diluted PPP was added to the plate and incubated for 1 hour at 37° C. ISTH Lot#3 was again used as a standard, with curve dilutions starting at 1:25 in substrate buffer, which was then serially diluted 1:2 to a final dilution of 1:1600. 2 μg/ml biotinylated AVW-1 and AVW-15 (Blood Research Institute) were added to the plate and incubated for 30 minutes at 37° C. Finally, streptavidin-conjugated alkaline phosphatase (Jackson ImmunoResearch Laboratories, Ltd.; West Grove, Pa.), diluted 1:5000 in substrate buffer, was added to the plate and incubated for 30 minutes at 37° C. p-Nitrophenyl Phosphate (PNPP; Invitrogen), an alkaline phosphate substrate, was diluted 1:100 in substrate buffer and added to the plate. The plate was read at 405/650 nm on a plate reader. The plate was washed three times between each step with PBS containing 0.05% Tween-20.

Results: As shown in Tables 7 and 8, individuals with normal VWF showed similar ELISA results whether ristocetin was added to the assay or not. In addition, the ELISA assay resulted in VWF measurements comparable to a method used in clinical laboratories

TABLE 7

Summary of VWF:IbCo by ELISA in Plasma Samples from African Americans and Caucasians with and without VWF Single Nucleotide Polymorphisms (SNPs).

| Subject | VWF:Ag | IbCo ELISA | Ristocetin ELISA | IbCo/VWF:Ag | Ris/VWF:Ag | Clinical VWF:Ag | VWF:RCo | VWF:RCo/VWF:Ag |
|---|---|---|---|---|---|---|---|---|
| ISTH 3 A | 121.25 | 109.4 | 127.3 | 0.90 | 1.05 | 106 | 86 | 0.81 |
| ctrl 5 (70%) | 75.62 | 68.97 | 69.68 | 0.91 | 0.92 | 742 | 60.2 | 0.81 |
| ctrl 6 (35%) | 32.28 | 31.12 | 28.76 | 0.96 | 0.89 | 37.1 | 30.1 | 0.81 |
| CCNRP 7122 A | 94.56 | 84.6 | 73.34 | 0.89 | 0.78 | 114 | 71 | 0.62 |
| ISTH 3 B | 96.71 | 99.71 | 104.05 | 1.03 | 1.08 | 106 | 86 | 0.81 |
| MK0038 | 33.44 | 1.41 | 14.16 | 0.04 | 0.42 | 47 | 11 | 0.23 |
| XX0017 | 139.5 | 157.35 | 169.5 | 1.13 | 1.22 | 206 | 200 | 0.97 |
| JS | 0 | 0.5 | 0.99 | 0.00 | 0.00 | <1 | <10 | 0.00 |
| ctrl 8 (30%) | 23.84 | 26.96 | 23.58 | 1.13 | 0.99 | 31.8 | 25.8 | 0.81 |
| ISTH 3 C | 85.14 | 94.42 | 90.48 | 1.11 | 1.06 | 106 | 86 | 0.81 |
| CCNRP 7122 B | 59.61 | 60.64 | 55.44 | 1.02 | 0.93 | 114 | 71 | 0.62 |
| AT0068 | 70.4 | 59.18 | 31.47 | 0.84 | 0.45 | 99 | 57 | 0.58 |

TABLE 8

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF/RCo | IbCo ELISA | Ristocetin ELISA | Clinical VWF:RCo/VWF:Ag | IbCo ELISA/BRI VWF:Ag |
|---|---|---|---|---|---|---|---|
| AA w/ 1380 + 1435 + 1472 | | | | | | | |
| HN | 334 | 228 | 165 | 165 | — | 0.494 | 0.725 |
| XX | 278 | 228 | 225 | 235 | 222 | 0.809 | 1.029 |
| AT | 257 | 309 | 248 | 234 | 220 | 0.965 | 0.759 |
| AT | 225 | 159 | 198 | 149 | 152 | 0.880 | 0.932 |
| AT | 225 | 172 | 95 | 67 | 106 | 0.422 | 0.393 |
| IN | 215 | 179 | 104 | 77 | 73 | 0.484 | 0.429 |
| XX | 193 | 200 | 140 | 123 | 154 | 0.725 | 0.616 |
| NO | 179 | 178 | 180 | 171 | — | 1.006 | 0.960 |
| AT | 103 | 83 | 69 | 58 | 64 | 0.670 | 0.701 |
| XX | 85 | 67 | 74 | 73 | 57 | 0.871 | 1.095 |

TABLE 8-continued

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF/RCo | IbCo ELISA | Ristocetin ELISA | Clinical VWF:RCo/VWF:Ag | IbCo ELISA/BRI VWF:Ag |
|---|---|---|---|---|---|---|---|
| AT | 71 | 65 | 72 | 70 | 53 | 1.014 | 1.077 |
| HN | 67 | 77 | 54 | 54 | — | 0.806 | 0.704 |
| AA w/ 1472 alone | | | | | | | |
| NO | 259 | 209 | 224 | 151 | 213 | 0.865 | 0.723 |
| XX | 195 | 129 | 130 | 118 | 132 | 0.667 | 0.910 |
| XX | 185 | 143 | 154 | 143 | 183 | 0.832 | 1.001 |
| XX | 167 | 172 | 170 | 123 | 198 | 1.018 | 0.714 |
| NO | 166 | 151 | 175 | 155 | — | 1.054 | 1.025 |
| IN | 153 | 123 | 146 | 120 | 55 | 0.954 | 0.970 |
| NO | 144 | 141 | 85 | 92 | — | 0.590 | 0.652 |
| DT | 141 | — | 121 | — | — | 0.858 | — |
| HN | 139 | — | 98 | — | — | 0.705 | — |
| XX | 137 | 112 | 123 | 90 | 151 | 0.898 | 0.801 |
| HN | 136 | 136 | 113 | 106 | — | 0.831 | 0.784 |
| XX | 122 | 89 | 85 | 75 | — | 0.697 | 0.839 |
| XX | 116 | 103 | 89 | 82 | 81 | 0.767 | 0.793 |
| XX | 110 | 104 | 91 | 100 | 62 | 0.827 | 0.967 |
| IN | 108 | 107 | 101 | 86 | 94 | 0.935 | 0.800 |
| AT | 99 | 91 | 57 | 50 | 25 | 0.576 | 0.550 |
| DT | 98 | 89 | 85 | 79 | 85 | 0.867 | 0.885 |
| AT | 84 | 96 | 79 | 82 | 63 | 0.940 | 0.856 |
| AA w/ no SNPs | | | | | | | |
| NO | 243 | 237 | 252 | 217 | — | 1.037 | 0.917 |
| PB | 234 | 192 | 211 | 110 | 83 | 0.902 | 0.576 |
| DT | 224 | 185 | 167 | 190 | — | 0.746 | 1.025 |
| AT | 199 | 178 | 193 | 177 | — | 0.970 | 0.993 |
| NO | 195 | 179 | 220 | 207 | 233 | 1.128 | 1.160 |
| AT | 164 | 132 | 151 | 98 | 96 | 0.921 | 0.743 |
| AT | 154 | 139 | 176 | 159 | 135 | 1.143 | 1.143 |
| IN | 122 | 76 | 85 | 68 | 74 | 0.697 | 0.897 |
| PB | 109 | 91 | 93 | 76 | 63 | 0.853 | 0.832 |
| PB | 86 | 63 | 88 | 64 | 52 | 1.023 | 1.025 |
| AT | 86 | 107 | 97 | 68 | 63 | 1.128 | 0.633 |
| AT | 86 | 57 | 69 | 60 | 56 | 0.802 | 1.055 |
| XX | 85 | 79 | 92 | 65 | 44 | 1.082 | 0.817 |
| AT | 82 | 93 | 94 | 70 | 49 | 1.146 | 0.750 |
| C w/ 1380 + 1435 + 1472 | | | | | | | |
| PB | 180 | 144 | 149 | 122 | 115 | 0.828 | 0.842 |
| IN | 94 | 91 | 84 | 68 | 79 | 0.894 | 0.747 |
| C w/ 1472 alone | | | | | | | |
| XX | 206 | 254 | 200 | 266 | 251 | 0.971 | 1.050 |
| IN | 192 | 137 | 144 | 133 | 126 | 0.750 | 0.973 |
| DT | 174 | 148 | 137 | 165 | 127 | 0.787 | 1.119 |
| IN | 171 | 106 | 122 | 94 | 127 | 0.713 | 0.888 |
| PB | 129 | 102 | 85 | 76 | 66 | 0.659 | 0.751 |
| IN | 111 | 88 | 99 | 76 | 78 | 0.892 | 0.861 |
| XX | 97 | 67 | 89 | 82 | 80 | 0.918 | 1.224 |
| HN | 94 | 103 | 82 | 82 | — | 0.872 | 0.791 |
| IN | 91 | 65 | 88 | 58 | 51 | 0.967 | 0.902 |
| C w/ no SNPs | | | | | | | |
| PB | 289 | 313 | 256 | 309 | 292 | 0.886 | 0.988 |
| IN | 237 | 171 | 255 | 154 | 275 | 1.076 | 0.901 |
| IN | 187 | 165 | 138 | 124 | 144 | 0.738 | 0.753 |
| XX | 129 | 121 | 149 | 90 | 112 | 1.155 | 0.745 |
| XX | 124 | 128 | 169 | 137 | 127 | 1.363 | 1.073 |
| IN | 103 | 82 | 92 | 67 | 78 | 0.893 | 0.815 |
| IN | 100 | 71 | 91 | 68 | 72 | 0.910 | 0.957 |
| XX | 96 | 93 | 109 | 132 | 103 | 1.135 | 1.425 |
| IN | 96 | 86 | 110 | 94 | 87 | 1.146 | 1.086 |
| XX | 94 | 77 | 101 | 74 | 83 | 1.074 | 0.972 |
| XX | 94 | 100 | 86 | 88 | 93 | 0.915 | 0.875 |
| DT | 88 | 90 | 107 | 91 | 83 | 1.216 | 1.008 |
| PB | 88 | 79 | 78 | 50 | 54 | 0.886 | 0.628 |
| IN | 85 | 61 | 77 | 58 | 57 | 0.906 | 0.961 |
| IN | 85 | 74 | 82 | 65 | 56 | 0.965 | 0.872 |

TABLE 8-continued

Summary of VWF:IbCo by ELISA in Plasma Samples from African Americans and Caucasians with and without VWF Single Nucleotide Polymorphisms (SNPs).

| Subject | Clinical VWF:Ag | BRI VWF:Ag | Clinical VWF/RCo | IbCo ELISA | Ristocetin ELISA | Clinical VWF:RCo/VWF:Ag | IbCo ELISA/BRI VWF:Ag |
|---|---|---|---|---|---|---|---|
| PB | 83 | 80 | 88 | 60 | 51 | 1.060 | 0.742 |
| DT | 82 | 73 | 79 | 65 | 63 | 0.963 | 0.891 |
| PB | 74 | 52 | 69 | 53 | 34 | 0.932 | 1.017 |
| DT | 68 | 57 | 71 | 55 | 56 | 1.044 | 0.956 |
| XX | 58 | 54 | 61 | 52 | 49 | 1.052 | 0.958 |

AA = African American
C = Caucasian

Thus, measurement of VWF function using a VWF:IbCo FACS or ELISA assay more directly correlates with VWF function and avoids some of the pitfalls and functional variability observed with VWF:RCo assays.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of measuring von Willebrand factor (VWF) without using a platelet agglutination agonist, the method comprising the steps of: providing a surface comprising immobilized platelet glycoprotein Ibα (GPibα) or a functional fragment thereof, wherein the immobilized GPibα or functional fragment thereof comprises a combination of mutations selected from G233V, D235Y and M239V relative to SEQ ID NO:2, wherein one of the mutations is D235Y; contacting a patient sample having or suspected of having VWF with the surface, wherein the contacting is done without a platelet aggregation agonist; and detecting a complex of VWF and GPibα.

2. The method of claim 1, wherein the surface is a host cell surface, and wherein the host cell does not natively express GPibα.

3. The method of claim 2, wherein the host cell for the host cell surface is selected from the group consisting of a Xenopus oocyte, a CHO-K1 cell, a L929 cell, a HEK-293T cell, a COS-7 cell and a S2 cell, and wherein the host cell is engineered to comprise a polynucleotide encoding the GPibα or functional fragment thereof.

4. The method of claim 2, wherein the host cell surface also comprises glycoprotein Ibβ (GPibβ) and optionally glycoprotein IX (GP-IX), wherein GPib β comprises SEQ ID NO:4 and GP-IX comprises SEQ ID NO:8.

5. The method of claim 1, wherein the surface is a solid-phase surface selected from the group consisting of agarose, glass, latex and plastic.

6. The method of claim 5, wherein the solid-phase surface comprises an anti-GPibα antibody that binds the GPibα or functional fragment thereof.

7. The method of claim 1, wherein the sample is plasma.

8. The method of claim 1, wherein the combination of mutations is D235Y/G233V or D235Y/M239V.

9. The method of claim 1, wherein the combination of mutations is D235Y/G233V/M239V.

10. The method of claim 1, wherein a labeled anti-VWF antibody is used to detect the complex of VWF and GPibα.

11. The method of claim 1, wherein the patient has or is suspected of having von Willebrand disease.

* * * * *